United States Patent
Bedate et al.

(10) Patent No.: US 6,962,704 B2
(45) Date of Patent: Nov. 8, 2005

(54) **CHIMERIC GENE FORMED BY THE DNA SEQUENCES THAT ENCODE THE ANTIGENIC DETERMINANTS OF FOUR PROTEINS OF *L. INFANTUM* AND PROTEIN ENCODED BY SAID GENE, AND PHARMACEUTICAL COMPOSITION USEFUL FOR PREVENTING AND/OR TREATING *LEISHMANIOSIS* IN ANIMALS OR HUMANS**

(75) Inventors: Carlos Alonso Bedate, Madrid (ES); Jose Maria Requena Rolania, Madrid (ES); Manuel Soto Alvarez, Madrid (ES)

(73) Assignee: Laboratories Leti S.L. Unipersonal, Madrid (ES)

( * ) Notice: Subject to any disclaimer, the term of this patent is extended or adjusted under 35 U.S.C. 154(b) by 2 days.

(21) Appl. No.: 10/237,040

(22) Filed: Sep. 9, 2002

(65) Prior Publication Data

US 2004/0022804 A1 Feb. 5, 2004

Related U.S. Application Data

(62) Division of application No. 09/471,396, filed on Dec. 23, 1999, now Pat. No. 6,458,359.
(60) Provisional application No. 60/113,825, filed on Dec. 23, 1998.

(51) Int. Cl.[7] .................. A61K 39/00; A61K 39/002; A61K 39/38
(52) U.S. Cl. .................. 424/184.1; 424/185.1; 424/265.1; 424/269.1
(58) Field of Search .................. 424/184.1, 185.1, 424/265.1, 269.1, 192.1, 191.2, 490, 268.1; 435/69.1, 7.92, 320.1, 7.22, 7.25, 7.99, 252.3; 536/23.2, 27.21; 530/324, 350; 514/46, 252.13

(56) References Cited

U.S. PATENT DOCUMENTS 5,719,263 A 2/1998 Reed 5,965,142 A 10/1999 Dillon et al.

OTHER PUBLICATIONS

Rudinger et al (Peptide Hormones, University Park Press, Jun. 1976, pp 1–7).*

Russo, D.M., et al. Nov. 15, 1991. Human T Cell Responses to gp63, a Surface Antigen of *Leishmania* J. Immun. vol. 147 [No. 10], pp. 3575–3580.*

Quijada, L. et al. 1996. During canine viscero–cutaneous leishmaniasis the anti–Hsp70 antibodies are specifically elicited by the Parisite Protein. Parisit. vol. 112, pp. 277–284.*

Skeiky, Y.A.W. 1994. Antigens Shared by *Leishmania* species and *Trypanosoma cruzi* : Immunological Comparison of the Acidic Ribsomal PO Proteins. Infect. and Immun. vol. 62[5], pp. 1643–1651.*

Bowie et al., Science, vol. 247:1990; p. 1306; p. 1308.

* cited by examiner

*Primary Examiner*—Mark Navarro
(74) *Attorney, Agent, or Firm*—Browdy and Neimark, PLLC

(57) ABSTRACT

Chimeric gene formed by the DNA sequences that encode the antigenic determinants of four proteins of *L. infantum*, useful for the serological diagnosis of canine *Leishmaniosis* and protein obtained, that consists of the prior employment of a cloning strategy. A clone is obtained which expresses the protein rLiPO-Ct-Q (pPQI). To this initial vector, by means of the use of suitable restriction targets, DNA fragments are sequentially added that are encoded in other proteins and after each cloning step the correct orientation of each one of the inserts reduces the size of the expression products, the complete nucleotide sequence of the final pPQV clone being determined. A chimeric polypeptide encoded by the chimeric gene is obtained with a molecular mass of 38 kD and with an isoelectric point of 7.37. This chimeric polypeptide is useful for preventing and/or treating *Leishmaniosis* in animals or humans.

1 Claim, 6 Drawing Sheets

Fig 3

MBP IEGRPLATPRSAKKAVRKSGSKSAKCGLIFPVGRVGGMMRRGQYARRIGA  50

SGAPRISEFSVKAAAQSGKKRCRLNPRTVMLAARHDDDIGTLLKNVTLSHSGVV  104

PNISKAMAKKKGGKKGKATPSAPEFGSSRPMSTKYLAAYALASLSKASPSQAD  157

VEAICKAVHIDVDQATLAFVMESVTGRDVATLIAEGAAKMSAMPAASSGAAAGV  211

TASAAGDAAPAAAAAKKDEPEEEADDDMGPSRVDPMQYLAAYALVALSGKTPSK  265

ADVQAVLKAAGVAVDASRVDAVFQEVEGKSFDALVAEGRTKLVGSGSAAPAGAV  319

STAGAGAGAVAEAKKEEPEEEEADDDMGPVDLQPAAAAPAAPSAAAKEEPEESD  373

EDDFGMGGLF

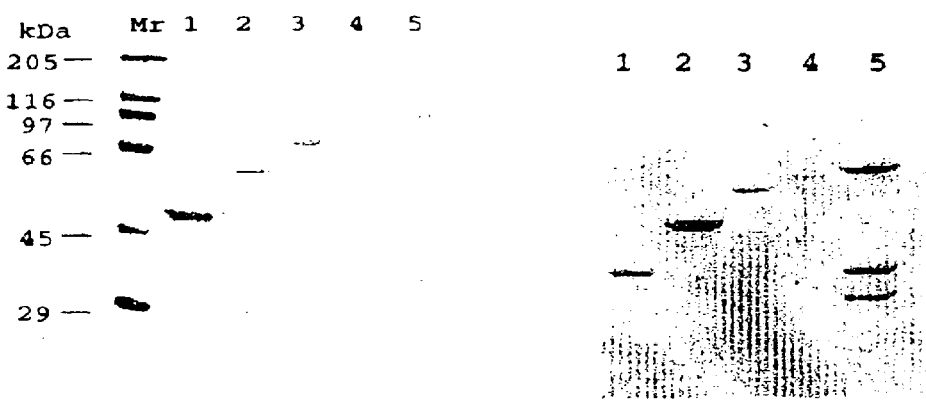

Fig 4a  Fig 4b

CHIMERIC GENE FORMED BY THE DNA SEQUENCES THAT ENCODE THE ANTIGENIC DETERMINANTS OF FOUR PROTEINS OF *L. INFANTUM* AND PROTEIN ENCODED BY SAID GENE, AND PHARMACEUTICAL COMPOSITION USEFUL FOR PREVENTING AND/OR TREATING *LEISHMANIOSIS* IN ANIMALS OR HUMANS

CROSS-REFERENCE TO RELATED APPLICATIONS

This is a divisional of parent application Ser. No. 09/471,396, filed Dec. 23, 1999, now issued as U.S. Pat. No. 6,458,359, which claims the benefit of U.S. Provisional Appln. No. 60/113,825, filed Dec. 23, 1998.

OBJECT OF THE INVENTION

The present specification relates to an application for an Invention Patent, regarding a chimeric gene formed of the DNA sequences that encode the antigenic determinants of four proteins of *L. infantum*, and to proteins encoded by said chimeric gene, useful for the prevention or treatment of leishmaniosis, in particular canine leishmaniosis. The obvious purpose of this lies in using the gene sequence or the protein obtained from the chimeric gene for providing pharmaceutical compositions for preventing or treating leishmaniosis, in particular canine leishmaniosis, that can be present in the body of a patient, for instance as a vaccine or a monoclonal antibody preparation. This patient does not have to be a dog but can also be a human being who suffers from diseases that involve immuno-depression. To achieve this, a chimeric gene will be produced that encodes a protein called PQ consisting of a chimeric product originating from an "in vitro" synthesis of a chimeric gene constructed "ad hoc", which contains five of the antigenic determinants of four different proteins. The product is configured as highly sensitive and specific for—for instance—generating a protective immune responds against canine Leishmaniosis, or for preparing antibodies against canine Leishmaniosis.

BACKGROUND OF THE INVENTION

1. Field of the Invention

This invention is of utility within the industry dedicated to the manufacture of pharmaceutical products in general.

2. Description of the Related Art

The parasitic protozoa of the *Leishmania* genus are the aetiological agents that cause Leishmaniosis, a range of diseases that have a world-wide distribution and that are characterised in that they give rise to a wide variety of clinical symptoms.

The main forms of Leishmaniosis are zoonotic in nature and humans are considered as secondary hosts.

The species denoted *L. Infantum*, widely distributed throughout many Mediterranean areas is the cause of visceral Leishmaniosis (LV) in humans and dogs.

In fact, dogs infected with *L. infantum* are the main animal reserve of this parasite, particularly during the long incubation period before the clinical symptoms can be observed.

The epidemiological data indicate that there is a direct correlation between the prevalence of canine Leishmaniosis and the transmission of the parasite to humans. For this reason, it is crucial to detect the disease or infection early on in campaigns undertaken to control the spread of the disease.

The parasite is transmitted to the host vertebrate as a flagellate promastigote, by means of a bite of a fly of the family "Phlebotominae", and the parasite enter the cells of the mononuclear phages where they differentiate and reproduce as, amastigotes, within the phago-lisosomal structure.

The infected cells gather in certain tissues, mainly spleen, liver and lymph nodes. It is estimated that around 15 million people are infected with Leishmaniosis, and every year in the world 500,000 new clinical cases appear in the world, mainly in the underdeveloped and developing world, In the south-western countries of Europe, Visceral Leishmaniosis (VL), is a zoonotic disease caused by the L. *Infantum* species, as was mentioned earlier. Recent data derived from epidemiological studies indicate that there is an alarming incidence of this infection.

In Italy the reported data for incidence of VL ranges from 14.4% to 37% according to the region.

In Portugal, more particularly in the area around Lisbon, seropositive rates of 8.4% have been found and in the region of the French Maritime Alps different centres of prevalence have been found that vary between 3.2% and 17.1%.

In Spain, the prevalence of Leishmaniosis depends on the zone being studied. In Catalonia an average incidence rate of 9.3% has been observed although in some hot-spots a prevalence of infected dogs of up to 18% has been found.

On the Island of Mallorca, the incidence rate is 14%, and other rates that have been found are: 2.4% in Murcia, 8.8% in Granada, from 10 to 15% in Salamanca, 5.25% in the province of Madrid, and 14% in Caceres.

Although the number of cases of VL in humans caused by *L. infantum* can be considered relatively low, the high percentage of patients with immuno-depression that become infected by *Leishmania* could be related to the high level of this illness in dogs.

In fact, in the South of Europe, 50% of adults that are infected by Leishmaniosis are also patients infected by the XIV virus. On the other hand, according to these data of *Leishmania*-HIV co-infection, it has been estimated that the level of infection (by parasites) can be one or two orders of magnitude higher than this figure due to the existence of a large number of undetected infections.

A common characteristic of the different types of *Leishmania infection* is that it induces a strong humoral response in the host. Therefore, diagnostic methods based on serological techniques are currently the most widely used.

It has been described that these antibodies are detected even during the asymptomatic phase of the disease in natural and experimental infections.

The sensitivity and specificity of these methods depends on the type, source and purity of the antigen used. In immunological processes that are currently commercialised, complete promastigotes and preparations more or less prepared from these are used as a source of antigen. This method normally leads to cross-reactions with serum from patients suffering from leprosy, tuberculosis, African tripanosomiasis, Chagas disease, malaria and other parasitosis.

The sensitivity and specificity of the serologic methods depend on the type, source and purity of the employed antigen. During the last years a great number of *Leishmania antigens* have been characterized, some of them can be considered as proteins specific to the parasite.

Among these proteins specific to the parasite, the surface protease CP63, the surface glycoprotein gp46 and the lipophosphoglicane associated KMP-11 protein deserve a mention.

An additional group of *Leishmania antigens* are formed of evolutionarily conserved proteins, such as kinesine, thermally induced proteins, actin and tubulin.

As part of a strategy to develop a specific serological diagnostic system for Leishmaniosis canine, a laboratory based project has been undertaken to identify the antigens of *L. infantum*, by means of a immuno-detection search of an expression library for genes of *L. infantum* using dog serum with active visceral Leishmaniosis.

It has been observed that most of the antigens isolated by this method belong to the family of proteins conserved during the course of evolution. The identification of the B epitopes of these antigens indicate, however, that in all cases the antigenic determinants were localised in regions that were not well conserved.

In particular, the acidic ribosomal proteins LiP2a and LiP2b are recognised by more than 80% of the VL sera.

It has been confirmed that these proteins contain disease specific antigenic determinants, and that the recombinant proteins LiP2a and LiP2b, from which a fragment had been removed, could be used as a specific instrument able to distinguish between VL and Chages disease.

It has also been shown that the PO ribosomal protein of *L. infantum*, very highly conserved on the evolutionary scale, is recognised by a high percentage of VL dog sera. Furthermore, the antigenic determinants are found exclusively on the C-terminus of the protein, that is to say, in the region that has been poorly conserved during the course of evolution.

It has been observed that in 78% of the VL dog sera, antibodies against H2A protein are also present, and it has been confirmed that despite the sequence identity in all the H2A proteins among eukaryotic organisms, the humoral response to this protein in VL sera is particularly provoked by determinants specific to the *Leishmania* protein H2A.

The antigenic determinants recognised by the VL dog sera are found at both termini of the H2A protein.

The obvious solution to the problem currently encountered in this art would be to have an invention that would allow the assembly of a synthetic chimeric gene that contained the DNA regions encoding the antigenic determinants specific to the proteins LiP2a, LiP2b, LiPO, and H2A, with a view to constructing a protein rich in antigenic determinants.

However, as far as the applicant is aware, there is currently no invention that contains the characteristics described as ideal, with a view to reaching the desired aim. This aim is the construction of a protein rich in antigenic determinants, arising from the assembly of a chimeric synthetic gene, that contains the DNA regions encoding the antigenic determinants specific to the aforementioned proteins.

SUMMARY OF THE INVENTION

In a first aspect, the invention relates to a chimeric gene formed by the DNA sequences that encode antigenic determinants of four proteins of *L. infantum*, useful for preventing or treating canine Leishmaniosis.

In a further aspect, the invention relates to a protein encoded by said chimeric gene, containing one or more of the antigenic determinants of four proteins of *L. infantum* encoded by the chimeric gene.

The invention further relates to method for preventing and/or treating canine Leishmaniosis in a human being or an animal. In this therapeutic method, the chimeric gene of the invention or the protein encoded by it can be used. Also, antibodies against the protein encoded by the chimeric gene of the invention, or a antigenic part thereof such as an epitope, can be used.

In further aspects, the invention relates to pharmaceutical compositions for the prevention and/or treatment, in humans and/or animals, of Leishmaniosis, comprising an active substance derived from or directed against the chimeric gene of the invention and/or the protein encoded by it, or parts thereof. The active substance is preferably such that it can be used in a pharmaceutical composition for the treatment and/or prevention of Leishmaniosis.

In particular, the pharmaceutical composition will be in a form of a vaccine, containing the protein encoded by the chimeric gene of the invention, or one or more parts thereof, containing one or more of the antigenic determinants of the protein encoded by the chimeric gene of the invention.

Thus, in a further aspect, the invention relates to a pharmaceutical composition for the prevention and treatment, human or animal, of leishmaniasis, formed:
a) by the protein Chimera Q, or a variant of this protein containing modifications or substitutions of preserved amino acids administered to a subject (human or animal), or
b) by protein Q in isolated form or combined with any physiological adjuvant by the intraperitoneal, subcutaneous or intramuscular route.

The invention also relates to a vaccine that is able to stimulate the production of antibodies that recognize the *Leishmania* parasite, formed
a) by the protein Chimera Q or a variant of this protein that differs from protein Q in preserved amino acids, administered to a subject (human or animal), or
b) by protein Q in isolated form or combined with a physiological adjuvant by the intraperitoneal, subcutaneous or intramuscular route.

Furthermore, the invention relates to a pharmaceutical composition for the prevention and treatment, human or animal, of leishmaniasis formed
a) by protein Q, or a variant of this protein containing modifications or substitutions of preserved amino acids, combined with the protein LiHsp70, complete or fragmented, administered to a subject (human or animal), or
b) by protein Q in isolated form or combined with a physiological adjuvant by the intraperitoneal, subcutaneous or intramuscular route.

In yet another aspect, the invention relates to a pharmaceutical composition for the prevention and treatment, human or animal, of leishmaniasis, formed
a) by any DNA vector bearing the sequence that codes for the protein Chimera Q, or a variant of that sequence that contains modifications or substitutions of nucleotides that code for preserved amino acids, administered to a subject (human or animal), or
b) by a DNA vector that contains protein Q combined with a physiological adjuvant, administered by the intraperitoneal, intramuscular or Subcutaneous route.

Another aspect of the invention relates to a pharmaceutical composition for the prevention and treatment, human or animal, of leishmaniasis, formed
a) by any DNA vector bearing:
  1) the sequence that codes for the protein Chimera Q, or a variant of that sequence that contains modifications or substitutions of nucleotides that code for preserved amino acids, and
  2) the sequence of nucleotides that codes for the protein LiHsp70 or variants thereof that differs with respect to preserved amino acids, administered to a subject (human or animal), or b) by any vector that contains the DNA sequence that codes for protein Q as defined under a) administered with a physiological adjuvant by the intraperitoneal, intramuscular or subcutaneous route.

In a further embodiment, the pharmaceutical composition of the invention comprises antibodies directed to the protein encoded by the chimeric gene of the invention, or parts thereof.

The pharmaceutical preparations of the invention may further contain all known adjuvants, solvents, buffers etc. known per se for pharmaceutical compositions and/or vaccines.

In a further aspect, the invention relates to a method for the treatment or prevention of Leishmaniosis, using a pharmaceutical composition or a vaccine according to the invention, or a preparation comprising antibodies directed against the protein encoded by the chimeric gene of the invention.

This method will generally comprise administering an active substance directed against the chimeric gene or the protein to a human being or animal, such as a dog, in a pharmaceutically active amount.

For the prevention of Leishmaniasis, a vaccine comprising the protein encoded by the chimeric gene, or encoding one or more parts of said protein comprising one or more of the antigenic determinants, will be administered to a human being to elicit a protective immune response.

Administration of the preparations, antibodies and/or vaccines of the invention may be carried out in a manner known per se, such as orally, intramuscularly, intravenously, subcutaneously, by (drip) infusion etc. Preferably, the preparation or a vaccine is injected, whereas with an antibody preparation, an infusion can be used.

It should be noted that when herein, reference is made to the chimeric gene of the invention, this term also encompasses nucleic acid sequences that can hybridize with the sequence mentioned below under moderate or stringent hybridizing conditions.

In this context, heterologous hybridisation conditions can be as follows: hybridisation in 6× SSC (20×SSC per 1000 ml:175.3 g NaCl, 107.1 g sodium citrate.5H$_2$O, pH 7.0), 0.1% . SDS, 0.05% sodium pyrophosphate, 5* Denhardt's solution (100× Denhardt's solution per 500 ml:10 g Ficoll-400, 10 g polyvinyl-pyrrolidone, 10 g Bovine Serum Albumin (Pentax Fraction V)) and 20 µg/ml denatured herring sperm DNA at 56° C. for 18–24 hrs followed by two 30 min. washes in 5×SSC, 0.1% SDS at 56° C. and two 30 min. washes in 2×SSC, 0.1% SDS at 56° C.

For instance, sequences that can hybridize with the sequence mentioned below include mutant DNA sequences which encode proteins with the same biological function as the protein encoded by the sequence mentioned hereinbelow. Such mutant sequences can comprise one or more nucleotide deletions, substitutions and/or additions to the sequence mentioned below. Preferably, the mutant sequences still have at least 50%, more preferably at least 70%, even more preferably more than 90% nucleotide homology with the sequence given hereinbelow.

The term chimeric gene as used herein also encompasses nucleic acid sequences that comprise one or more parts of the sequence mentioned hereinbelow. Preferably, such sequences comprise at least 10%, more preferably at least 30%, more preferably at least 50% of the nucleotide sequence given hereinbelow. Such sequences may comprise a contiguous fragment of the sequence mentioned hereinbelow, or two or more fragments of the sequence given below that have been combined in and/or incorporated into a single DNA sequence.

It should be noted that when herein, reference is made to a protein encoded by the chimeric gene of the invention, this term also includes mutant proteins that still essentially have the same biological function. Such mutant proteins can comprise one or more amino acid deletions, substitutions and/or additions compared to the protein encoded by the sequence mentioned below. Preferably, the mutant proteins still have at least 50%, more preferably at least 70%, even more preferably more than 90% amino acid homology with the sequence given hereinbelow.

The term protein also encompasses fragments of the protein encoded by the chimeric gene of the invention. Such fragments preferably still show the biological activity of the full protein. Preferably, such proteins comprise at least 30%, more preferably at least 50% of the amino acid sequence of the full protein. Also, two or more fragments of the full protein encoded by the chimeric gene of the invention may be combined to form a single protein.

More specifically, the invention relates to a chimeric gene formed by the DNA sequences that encode antigenic determinants of four proteins of L. infantum, encoding a protein useful for pharmacological purposes, in particular for the prevention and/or treatment of Leishmaniosis, in particular canine Leishmaniosis, and obtaining the final product or the construction of the chimeric gene that encodes a polypeptide that contains all the selected antigenic determinants, characterised in that it uses a cloning strategy in which the clone that expresses the protein rLiPO-Ct-Q is used as an initial vector, and to this vector, by means of the use of suitable restriction sites, fragments of DNA are sequentially added that encode the proteins LiP2a-Q, LiP2b-Q, LiH2A-Ct-Q, LiH2A-Nt-Q, and after each step of cloning the correct orientation of each one of the inserts is deduced and the -size of the expression products, the complete deduced sequence of amino acids of the final fusion protein, pPQV, expressed in the pMal vector is:

```
MBP                                                                    50   (SEQ ID NO.3)
IEGRPLATPRSAKKAVRKSGSKSAKCGLIFPVGRVGGMMRRGQYARRIGA

SGAPRISEFSVKAAAQSGKKRCRLNPRTVMLAARHDDDIGTLLKNVTLSHSGVV  104

PNISKAMAKKKGGKKGKATPSAPEFGSSRPMSTKYLAAYALASLSKASPSQAD   157

VEAICKAVHIDVDQATLAFVMESVTGRDVATLIAEGAAKMSAMPAASSGAAAGV  211

TASAAGDAAPAAAAAKKDEPEEEADDDMGPSVRDPMQYLAAYALVALSGKTPSK  265

ADVQALVKAAGVAVDASRVDAVFQEVEGKSFDALVAEGRTKLVGSGSAAPAGAV  319
```

-continued

STAGAGAGAVAEAKKEEPEEEEADDDMGPVDLQPAAAAPAAPSAAAKAAPEESD 373

EDDFGMGGLF

The invention also relates to a pharmaceutical composition for the prevention and treatment, in humans or animals, of Leishmaniasis formed:
a—by the protein Chimera Q, or a variant of this protein which contains modifications or substitutions of conserved amino acids, administered to a subject (human or animal), either
b—in isolated form or together with any physiological adjuvant via the intraperitoneal subcutaneous or intramuscular routes.

Also, the invention relates to a vaccine capable of stimulating the production of antibodies which recognise the *Leishmania* parasite, formed
a—by the protein Chimera Q or a variant of this protein which differs from protein Q in conserved amino acids administered to a subject (human or animal), either
b—in isolated form or together with any physiological adjuvant via the intraperitoneal, subcutaneous or intramuscular routes.

Another aspect of the invention comprises a pharmaceutical composition for the prevention and treatment, in humans or animals, of Leishmaniasis formed:
a—by protein Q, or a variant of this protein which contains modifications or substitutions of conserved amino acids, bound to protein LiHsp70, complete or fragmented, administered to a subject (human or animal), either
b—in isolated form or together with any physiological adjuvant via the intraperitoneal, subcutaneous or intramuscular routes.

A further pharmaceutical composition of the invention for the prevention and treatment, in humans or animals, of Leishmaniasis can be formed:
a—by any DNA vector carrying the sequence which encodes the protein Chimera Q, or a variant of this sequence which contains modifications or substitutions of nucleotides which code for conserved amino acids, administered to a subject (human or animal), either
b—by the intramuscular or subcutaneous routes.

In yet another aspect, the invention relates to a pharmaceutical composition for the prevention and treatment, in humans or animals, of Leishmaniasis formed:
a—by any DNA vector carrying 1—the sequence which encodes the protein Chimera Q, or a variant of this sequence which contains modifications or substitutions of nucleotides which code for conserved amino acids, and 2—the sequence which encodes the protein LiHsp70, or variants of the same which differ in conserved amino acids, administered to a subject (human or animal), either
b—by the intramuscular, subcutaneous or intramuscular route.

The invention also relates to a nucleotide sequence and to a protein useful for pharmacological purposes, in particular for the prevention and/or treatment of Leishmaniosis, in particular canine Leishmaniosis, having the DNA and amino acid sequence as shown below expressed in the vector PQ31. The amino acid sequence contains a fragment from the vector (AA 1–37) The rest of the amino acid sequence is identical to that of SEQ ID NO 3 except in the MBP moiety and the first seven amino acids (AA 1–7):

```
                                              (SEQ ID NO.1 and SEQ ID NO.2)
1                                                                        45
ATG AGA GGA TCT CAC CAC CAC CAC CAC CAC ACG GAT CCG CAT GCG
Met Arg Gly Ser His His His His His His Thr Asp Pro His Ala
                    5                   10                  15

46                                                                       90
AGC TCG AAC AAC AAC AAC AAT AAC AAT AAC AAC AAC CTC GGG ATC
Ser Ser Asn Asn Asn Asn Asn Asn Asn Asn Asn Asn Leu Gly Ile
                    20                  25                  30

91                                                                      135
GAG GGA AGG CCT TTA GCT ACT CCT CGC AGC GCC AAG AAG GCC GTC
Glu Gly Arg Pro Leu Ala Thr Pro Arg Ser Ala Lys Lys Ala Val
                    35                  40                  45

136                                                                     180
CGC AAG AGC GGC TCC AAG TCC GCG AAA TCT GCT CTG ATC TTC CCG
Arg Lys Ser Gly Ser Lys Ser Ala Lys Cys Gly Leu Ile Phe Pro
                    50                  55                  60

181                                                                     225
GTG GGC CGC GTC GGC GGG ATG ATG CGC CGC GGC CAG TAG GCT CGC
Val Gly Arg Val Gly Gly Met Met Arg Arg Gly Gln Tyr Ala Arg
                    65                  70                  75

226                                                                     270
CGC ATC GGT GCC TCT GGC GCC CCC AGG ATT TCA GAA TTC TCC GTG
Arg Ile Gly Ala Ser Gly Ala Pro Arg Ile Ser Glu Phe Ser Val
                    80                  85                  90

271                                                                     315
AAC GCG GCC GCG CAG AGC GGG AAG AAG CGG TGC CGC CTG AAC CCG
Lys Ala Ala Ala Gln Ser Gly Lys Lys Arg Cys Arg Leu Asn Pro
                    95                  100                 105
```

-continued

```
316                                                         360
CGC ACC GTG ATG CTG GCC GCG CGC CAC GAC GAC GAC ATC GGC ACG
Arg Thr Val Met Leu Ala Ala Arg His Asp Asp Asp Ile Gly Thr
                110                 115                 120

361                                                         405
CTT CTG AAG AAC GTG ACC TTG TCT CAC AGC GGC GTT GTG CCG AAC
Leu Leu Lys Asn Val Thr Leu Ser His Ser Gly Val Val Pro Asn
                125                 130                 135

406                                                         450
ATC AGC AAG GCG ATG GCA AAG AAG AAG GGC GGC AAG AAG GGC AAG
Ile Ser Lys Ala Met Ala Lys Lys Lys Gly Gly Lys Lys Gly Lys
                140                 145                 150

391                                                         495
GCG ACA CCG AGC GCG CCC GAA TTC GGA TCC TCT AGA CCC ATG TCC
Ala Thr Pro Ser Ala Pro Glu Phe Gly Ser Ser Arg Pro Met Ser
                155                 160                 165

496                                                         540
ACC AAG TAC CTC GCC GCG TAC GCT CTG GCC TCC CTG AGC AAG GCG
Thr Lys Tyr Leu Ala Ala Tyr Ala Leu Ala Ser Leu Ser Lys Ala
                170                 175                 180

541                                                         585
TCC CCG TCT CAG GCG GAC GTG GAG GCT ATC TGC AAG GCC GTC CAC
Ser Pro Ser Gln Ala Asp Val Glu Ala Ile Cys Lys Ala Val His
                185                 190                 195

596                                                         630
ATC GAC GTC GAC CAG GCC ACC CTC GCC TTT GTG ATG GAG AGC GTT
Ile Asp Val Asp Gln Ala Thr Leu Ala Phe Val Met Glu Ser Val
                200                 205                 210

641                                                         675
ACG GGA CGC GAC GTG GCC ACC CTG ATC GCG GAG GGC GCC GCG AAG
Thr Gly Arg Asp Val Ala Thr Leu Ile Ala Glu Gly Ala Ala Lys
                215                 220                 225

676                                                         720
ATG AGC GCG ATG CCG GCG GCC AGC TCT GGT GCC GCT GCT GGC GTC
Met Ser Ala Met Pro Ala Ala Ser Ser Gly Ala Ala Ala Gly Val
                230                 235                 240

721                                                         765
ACT GCT TCC GCT GCG GGT GAT GCG GCT CCG GCT GCC GCC GCC GCG
Gly Asp Ala Ala Pro Ala Ala Ala Ala Lys Lys Asp Glu Pro
                245                 250                 255

766                                                         810
AAG AAG GAC GAG CCC GAG GAG GAG CCC GAC GAC GAC ATG GGC CCC
Thr Ala Ser Ala Ala Glu Glu Glu Ala Asp Asp Asp Met Gly Pro
                260                 265                 270

811                                                         855
TCT AGA GTC GAC CCC ATG CAG TAC CTC GCC GCG TAC GCC CTC GTG
Ser Arg Val Asp Pro Met Gln Tyr Leu Ala Ala Tyr Ala Leu Val
                275                 280                 285

856                                                         900
GCG CTG TCT GGC AAG ACG CCG TCG AAG GCG GAC GTT CAG GCT GTC
Ala Leu Ser Gly Lys Thr Pro Ser Lys Ala Asp Val Gln Ala Val
                290                 295                 300

901                                                         945
CTG AAG GCC GCC GGC GTT GCC GTG GAT GCC TCC CGC GTG GAT GCC
Leu Lys Ala Ala Gly Val Ala Val Asp Ala Ser Arg Val Asp Ala
                305                 315                 315

946                                                         990
GTC TTC CAG GAG GTG GAG GGC AAG AGC TTC GAT GCG CTG GTG GCC
Val Phe Gln Glu Val Glu Gly Lys Ser Phe Asp Ala Leu Val Ala
                320                 325                 330

991                                                         1035
GAG GGC CGC ACG AAG CTG GTG GGC TCT GGC TCT GCC GCT CCT GCT
Glu Gly Arg Thr Lys Leu Val Gly Ser Gly Ser Ala Ala Pro Ala
                335                 340                 345
```

-continued

```
1036                                                        1080
GGC GCT GTC TCC ACT GCT GGT GCC GGC GCT GGC GCG GTG GCC GAG
Gly Ala Val Ser Thr Ala Gly Ala Gly Ala Gly Ala Val Ala Glu
                350                 355                 360

1081                                                        1125
GCG AAG AAG GAG GAG CCC GAG GAG GAG GAG GCC GAG GAT GAC ATG
Ala Lys Lys Glu Glu Pro Glu Glu Glu Glu Ala Asp Asp Asp Met
                365                 370                 375

1136                                                    1170
GGC CCC GTC GAC CTG CAG CCC GCC GCT GCC GCG CCG GCC GCC CCT
Gly Pro Val Asp Leu Gln Pro Ala Ala Ala Ala Pro Ala Ala Pro
                380                 385                 390

1171                                                    1215
AGC GCC GCT GCC AAG GAG GAG CCG GAG GAG AGC GAC GAG GAC GAC
Ser Ala Ala Ala Lys Glu Glu Pro Glu Glu Ser Asp Glu Asp Asp
                395                 400                 405

TTC GGC ATG GGC GGT CTC TTC TAAGCGACTC GCCATCTCTT       1256
Phe Gly Met Gly Gly Leu Thr
                410     412

1257
AGCCTCCTTG TGGTGCGCTT GAGGTGCTCT CGCTCTGCTT CTCCTTGCAG 1306

1307
TGTTGGCTGA CTCTGGCGGG TATGTGCCGT CGCATTACAC CCACCTCTCC 1356

1357
CACCCCTTTG CCCTACGCGC TCGCATGCGC AATCCGGGAA TCATCGAGGG 1406

1407
AAGTCTCTCT GGGTGGCAGT GGGTAAGCTT 1436
``` or a mutant or fragment thereof that can be used for generating a protective immune response in a human or animal against Leishmaniosis, and to a pharmaceutical composition for the prevention and treatment, in humans or animals, of Leishmaniosis, comprising this protein or a mutant or fragment thereof that can be used for generating a protective immune response in a human or animal against Leishmaniosis. This protein is derived from the insertion of gene PQV in the expression vector pQE31. Here said chimeric gene preferably encodes a polypeptide generated with a molecular weight of 38 kD and an isoelectric point of 7.37.

The protein used for the diagnosis extracted from the chimeric gene is identified, and the nucleotide sequence encoding said protein, are as follows:

Also, the invention relates to a vaccine capable of stimulating the production of antibodies which recognise the *Leishmania* parasite, comprising the protein mentioned above or a mutant or fragment thereof that can be used for generating a protective immune response in a human or animal against Leishmaniosis.

A further aspect of the invention encompasses a pharmaceutical composition for the prevention and treatment, in humans or animals, of Leishmaniasis, comprising antibodies directed against the protein mentioned above or a mutant or fragment thereof, preferably containing one or more antigenic determinants such as an epitope.

The invention further relates to a method for the prevention or treatment of Leishmaniosis in a human or animal, comprising administering to the human or animal a pharmaceutical composition as described above, or to a method for preventing Leishmaniosis in a human or animal, comprising administering to the human or animal a vaccine as described above.

The chimeric gene formed of the DNA sequences that encode the antigenic determinants of four proteins of *L. infantum* and protein obtained, useful for preventing and/or treating Leishmaniosis, that the invention proposes, in its own right constitutes an obvious novelty within its field of application, as according to the invention, a synthetic chimeric gene is produced that as it is obtained by assembly, containing the DNA region encoding the antigenic determinants specific to the proteins LiP2a, LiP2b, LiPO and H2A, thus constructing a protein rich in antigenic determinants. The chimeric gene obtained is expressed in *Escherichia coli* and the product has been analysed with respect to its antigenic properties. The results confirm that this chimeric protein maintains all the antigenic determinants of the parent proteins and that it constitutes a relevant pharmaceutically useful element for canine VL, with a sensibility that oscillates between 80% to 93%, and a specificity of between 96% to 100%.

More particularly, the chimeric gene formed by the DNA sequences that encode the antigenic determinants of four proteins of *L. infantum* and the protein encoded by it, useful for the prevention and/or treatment of canine Leishmaniosis and protein obtained object of the invention, is produced by means of the following stages, namely Construction of the chimeric gene, Methodology.
  Cloning strategy.
  Cloning of DNA sequences that encode antigenic determinants of the histone protein H2A.
  Cloning of the sequences that encode rLiP2a-Q and rLiP2b-Q.
  Cloning of the sequence rLiPO-Q.
  Cloning of the chimeric gene.
    Construction of the chimeric gene from the construction of intermediate products.
    Cloning of epitopes specific to the *L. infantum* antigens.
    Construction of the final product
    Construction of the chimeric gene that encodes a polypeptide that contains all the selected antigenic determinants.

optionally expression of the sequence thus obtained.
Evaluation of the final product.
Sera.
Purification of proteins
Electrophoresis of proteins and immuno-analysis.
Measurements by Fast-ELISA
Evaluation of the final product.
Antigenic properties.
Sensitivity and specificity of the chimeric protein CP in the serum diagnosis of canine VL.

The strategy followed by the cloning of DNA sequences that encode each one of the selected antigenic determinants is the same in all cases, and in a first step, the sequence of interest is amplified by means of a PCR and the use of specific oligonucleotides that contain targets for restriction enzymes at the extremes.

For the cloning step, the amplified product is directed by means of the appropriate restriction enzyme and it is inserted in the corresponding restriction site of the plasmid pUC18.

After sequencing the DNA, the insert is recovered and sub-cloned to the corresponding restriction site of the modified plasmid denominated pMAL-c2. The modification is made by inserting a termination codon downstream of the target HindIII in the polylinker of pMal-c2, denominating the resulting plasmid pMAL-c2.

Regarding the cloning of the DNA sequence that encodes the antigenic determinants of the histone protein H2A, it should be pointed out that the cDNA of the clone cL71, that encodes the histone H2A of *L. infantum*, is used as a template for the PCR reactions, and for the DNA amplification, that encodes the N-terminal region of the histone H2A, more exactly the N-terminal region of the histone H2A, more exactly rLiH2A-Nt-Q, the following oligonucleotides are used: sense 5'-CCTTTAGCTACTCCTCGCAGCGCCAAG-3' (SEQ ID NO:4) (position 84–104 of the sequence cL71); antisense 5'-CCTGGGGGCGCCAGAGGCACCGATGCG3' (SEQ ID NO:5) (inverse and complimentary to position 204–224 of the sequence cL71).

The sequences that are included in the oligonucleotides for the cloning and that are not present, in the parent sequence cL-71 are marked in boldface type.

The amplified DNA fragment is cloned directly from the restriction site XmnI of pMAI-c2*.

The fragment is sequenced by means of the initiator #1234 ma1E and the antigenic C-terminal region of histone H2A, in particular rLiH2A-Ct-Q, is amplified with the following oligonucleotides, These are:

Sense, 5'-GAATTCTCCGTAAGGCGGCCGCGCAG-3' (SEQ ID NO:6) (position 276–296 of the sequence cL71).

Antisense, 5'-GAATTCGGGCGCGCTCGGTGTCGCCTTGCC-3' (SEQ ID NO:7) (inverse and complimentary to the positions 456–476 of the plasmid cL71).

A triplet that encodes proline (indicated as GGG after the underlined letters) is included in the anti-sense oligonucleotide, the restriction site EccRI that is included in both oligonucleotides for cloning is indicated by underlining.

Regarding the cloning of the sequences that encode rLiP2a-Q, it should be pointed out that the regions of interest are amplified by PCR from cDNAs encoding LiP2a and LiP2b.

The oligonucleotides that are used for constructing the expression clone LiP2a-Q, are the following.

Sense, 5'-GTCGACCCCATGCAGTACCTCGCCGCGTAC-3' (SEQ ID NO:8)

Anti-sense, 5'-GTCGACGGGGCCCATGTCATCATCGGCCTC-3' (SEQ ID NO:9).

It should be pointed out that the SalI restriction sites added to the 5' extremes of the oligonucleotides have been underlined.

When constructing the expression clone LiP2b-Q, the oligonucleotides used were:

Sense, 5'-TCTAGACCCGCCATGTCGTCGTCTTCCTCGCC-3' (SEQ ID NO:10)

Anti-sense, TCTAGAGGGGCCATGTCGTCGTCGGCCTC-3' (SEQ D NO:11).

At the 5' extremes of the oligonucleotides the restrictions sites are included for the enzyme XbaI (underlined), and due to the cloning needs, an additional triplet, encoding a praline residue, is included downstream of the restriction site.

Regarding the cloning of the sequence rLiPO-Q, it should be pointed out that the cloning of the DNA sequence of the C-terminal region of the protein PO of *L. infantum* is carried out by amplifying a clone of cDNA called L27 and the following oligonucleotides:

Sense, 5'-CTGCAGCCCGCCGCTGCCGCGCCGGCCGCC-3' (SEQ ID NO:12) (positions 1–24 of the L27 cDNA) and the initiator of the pUC18 sequence (#1211), the amplified DNA is directed by the enzymes PstI+HindIII, with later insertion into the plasmid pMAL-c2.

The resulting clone is denominated pPQI and it should be noted that the restriction site PstI is included in the nucleotide with sense (underlined sequence) and that the restriction target HindIII is present in the cDNA L27.

Regarding the cloning of the chimeric gene, it should be pointed out that the DNA sequences that encode the five antigenic determinants are assembled into a chimeric gene, and this assembly is carried out on the clone pPQI, to which the codifying regions for the antigenic regions LiP2a-Q are added sequentially in the 31 direction (naming the results of cloning pPQII), LiP2b-Q (clone pPQIII), LiH2a-Ct-Q (clone pPQIV) and LiH2A-Nt-Q (clone pPQV).

Finally, the insert obtained after the SacI+HindIII digestion of the final clone pPQV is inserted into the pQE31 expression plasmid, naming the resulting clone pPQ.

BRIEF DESCRIPTION OF THE DRAWINGS

To complete the description that is being made and with the aim of aiding the understanding of the characteristics of the invention, the present disclosure is accompanied, as an integral part thereof, by a set of plans of illustrative nature that are not limiting. The following is represented:

FIG. 3. Corresponds to the identification of the protein obtained from the chimeric gene fused to the MBP protein, the preparation of which is represented in FIG. 2.

F: ELISA) of the intermediates and of the final chimeric protein fused to the maltose binding protein (PQI-PGV). The figure also represents the expression of the chimeric protein (D lane 1), purification in Ni-Nt agarose columns (D lane 2) and the antigenicity of the purified protein against a VL serum (E: Western blot) and against a collection of sera (F: PQ in ELISA).

Figure 5:
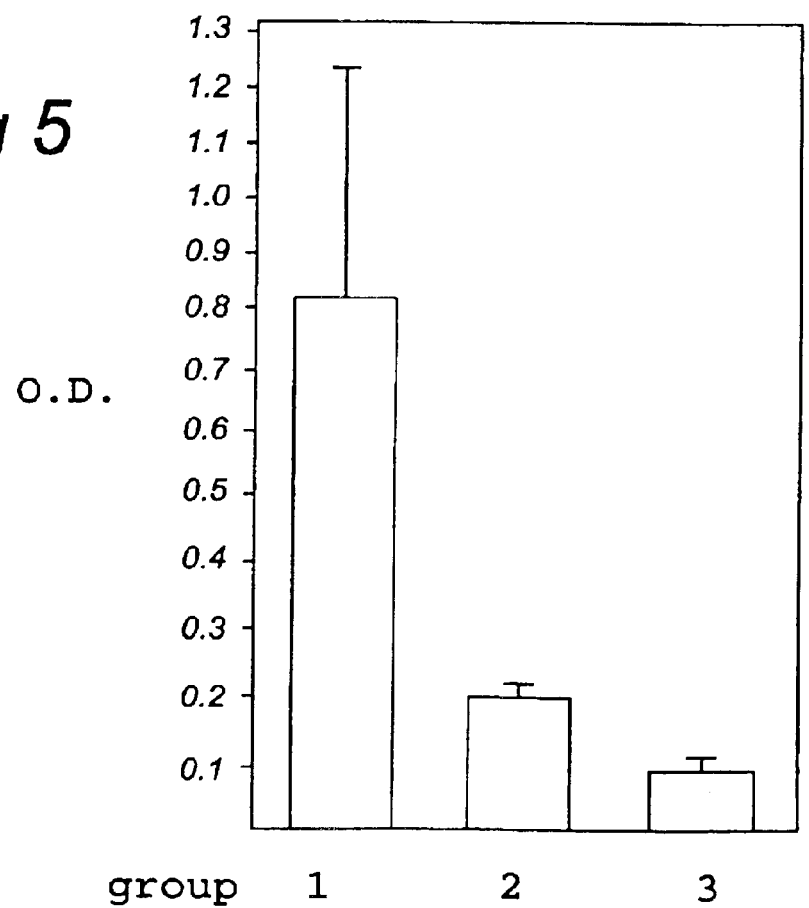

FIG. 5. Shows finally a synthesised graphical representation of the reactivity of a wide variety of canine sera, divided into three groups. The first group contain animals with real infection by *L. infantum*. The second group includes serum obtained from dogs with various clinical symptoms but that are not infected with *Leishmania*, and a third group is made up of fifteen control sera from healthy dogs. This figure demonstrates the value of the invention for carrying out serological diagnosis of VL.

PREFERRED EMBODIMENT OF THE INVENTION

The chimeric gene formed from the DNA sequences that encode the antigenic determinants of four proteins of *L. infantum*, useful for the serological diagnosis of canine Leishmaniosis and the protein obtained that is being proposed are constituted from the construction of intermediate products. In a first instance, cloning of epitopes specific to the antigens of *L. infantum* is carried out, which is configured on the basis of earlier studies on the antigenic properties of four protein antigens of *L. infantum* (LiP2a, PiPO, LiP2b, LiH2a), which allow the existence of B epitopes to be defined for these proteins, and which are specifically recognised by the canine sera of VL.

With a view to improving the antigenic specificity of these antigens with respect to the proteins of *L. infantum*, the specific antigenic determinants are cloned from these proteins. After deleting certain regions of these proteins these can be recognized by sera from animals that are carriers of VL and other different diseases.

By using the specific oligonucleotides and amplification by PCR of regions specific to the genes LiP2a, LiP2b, P0 and H2A, several clones are constructed that express the recombinant proteins rLiPO-Ct-Q, rLiP2a-Q, rLiP2b-Q, rLiH2A-Ct-Q and rLiH2A-Nt-Q, just has been detailed in the description of the invention relating to the methodology, where the cloning details are described.

The recombinant proteins used are the following;

rLiPO-Ct-Q, which corresponds to the 30 C-terminal residues of the ribosomal protein LiPO.

rLiP2a-Q and rLiP2b-Q, that are derived from the ribosomal proteins LiP2a and LiP2b respectively.

Two sub-regions of the histone H2A, that correspond to the 46 N-terminus residues (xLiH2A-Nt-Q), and to the 67 C-terminus residues (residues (xLiH2A-Ct-Q).

Each one of the recombinant proteins fused to the maltose binding protein (MBP) is expressed in *E. Coli*, as represented in Figure number 1A, and they were purified by affinity chromatography on a amylose column B. After the process of-purification-electrophoresis was carried out on the recombinant proteins.(lanes 1 to 5).

With the aim of analysing whether the recombinant proteins were recognised by VL canine sera, a Western blot was incubated, containing the recombinant proteins in a mixture of three, VL canine sera. Given that all these proteins are recognised by the sera, it is concluded that the antigenic determinants present in the parent proteins are maintained in the recombinant proteins (C).

The antigenic properties of the recombinant proteins are compared with the antigenic-determinants of the parent antigens by means of a, FAST ELISA, testing against a collection of 26 VL canine sera, just as is shown in the section of Figure number 1D, and the fact that the sera showed a similar reactivity value, both against the selected antigenic regions and the corresponding complete proteins, demonstrates that no alteration to the antigenic epitope has occurred during the cloning procedure.

Figure 1A:
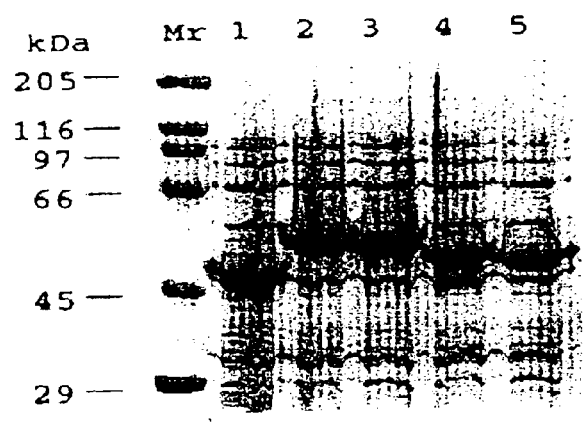
FIG. 1. Corresponds to the expression (A), purification in amylose columns (B) and the antigenicity (C: Western blot; D: ELISA) of each one of the recombinant proteins fused to the maltose binding protein. The figure under D also presents the reactivity in ELISA of each one of the recombinant protein relative to the complete protein.
Figure 1B:
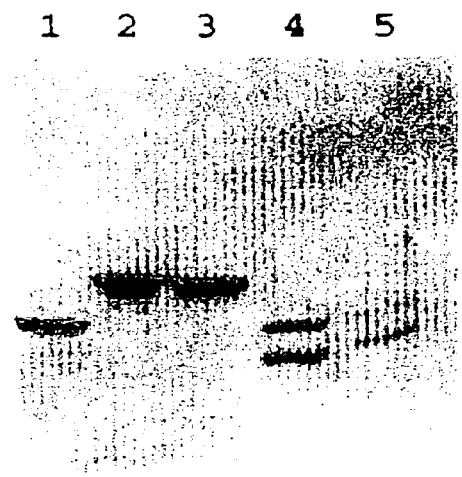
Figure 1C:
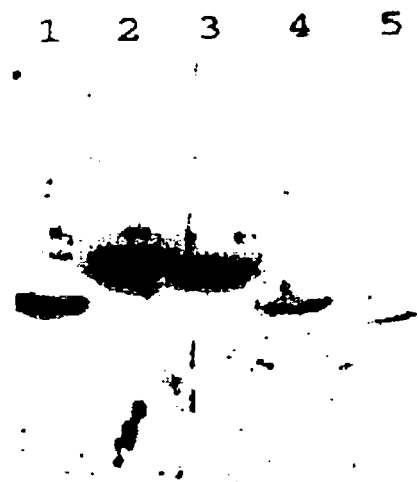
Figure 1D:
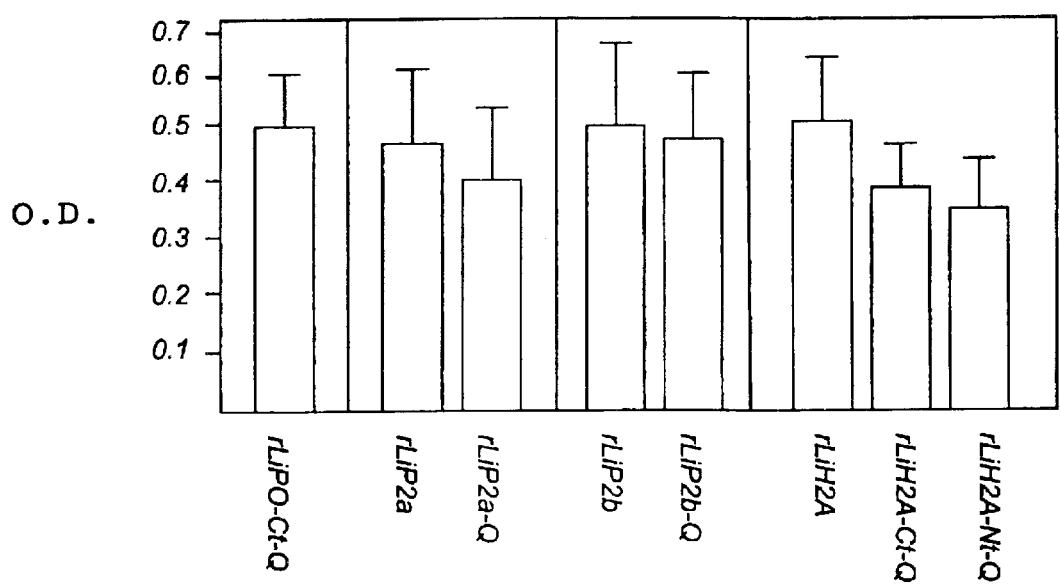
Figure 2:
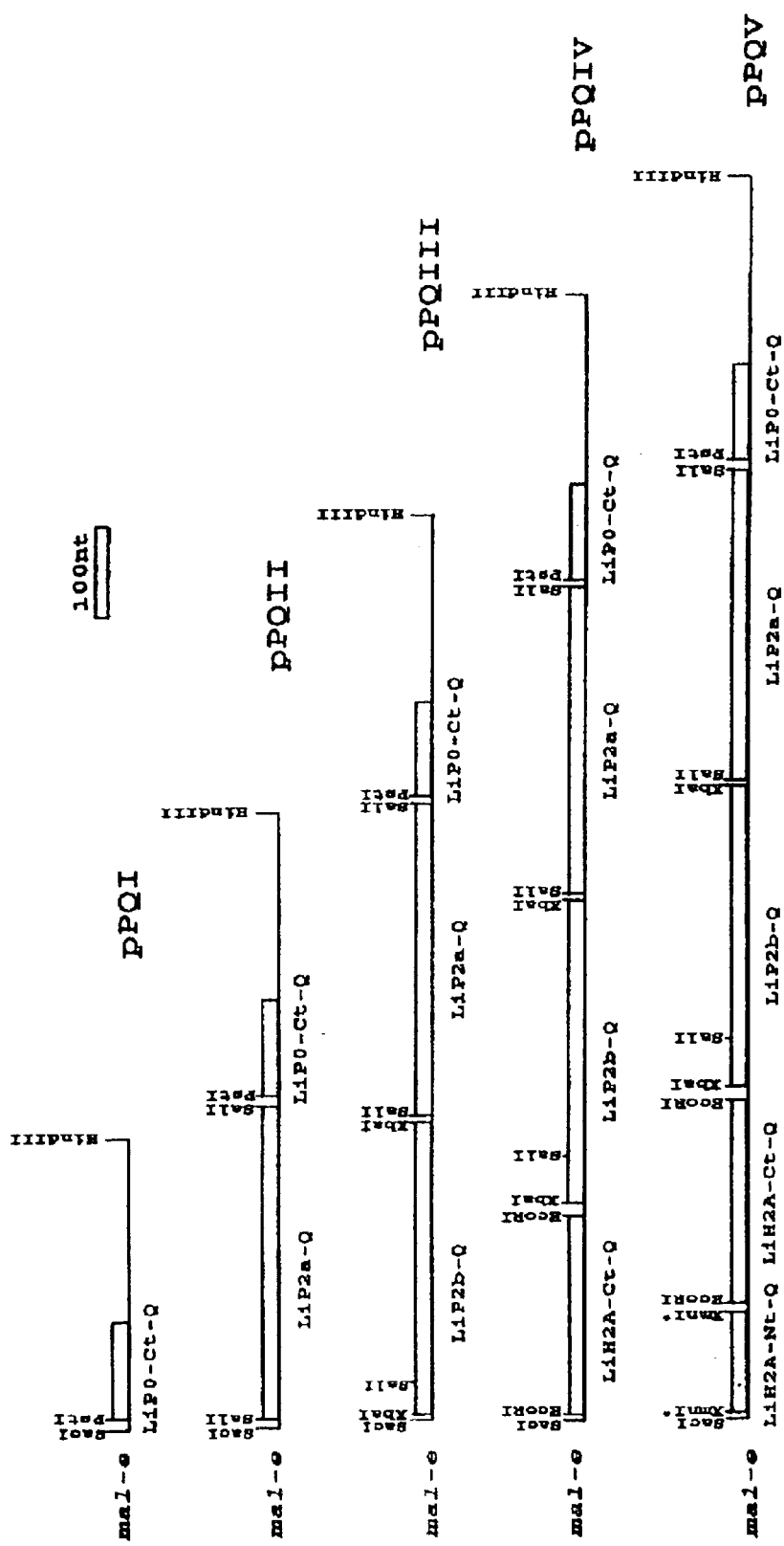
FIG. 2. Graphic representation of the different vectors considered to obtain the chimeric gene object of the invention, from which the pertinent protein destined to carry out an accurate diagnostic on animals or human beings that show symptoms of Leishmaniosis will be extracted.

In regard to the construction of the final product, more exactly of the chimeric gene that encodes a polypeptide that contains all the selected antigenic determinants, it should be pointed out that the cloning strategy is indicated following FIG. 2 section A.

The intermediate products generated during the process are shown.

A clone that expresses the proteins rLiPO-Ct-Q (pPQI) is used as the initial vector, and the fragments of DNA that encode the proteins rLiPO-Ct-Q, rLiP2a-Q, rLiP2b-Q, rLiH2A-Ct-Q and rLiH2A-Nt-Q are added sequentially using appropriate restriction sites.

After each cloning step, the correct orientation of each one of the inserts is deduced from the size of the expression products, and finally the complete nucleotide sequence of the final clone pPQV is determined and the amino acid sequence deduced from the sequence represented in FIG. 3.

The polypeptide generated has a molecular mass of 38 kD, with an isoelectric point of 7.37, including spacer sequences encoding proline, underlined in FIG. 3.

The aim of doing this is to efficiently separate the antigenic domains and avoid possible tertiary conformations that could interfere with the stability and antigenicity of the final product.

The expression and recovery of each of the intermediate products is shown in FIG. 4, boxes A and B. As was expected, after each addition, the size of the expression product in the vector pMAL gradually increases until reaching a molecular weight of 80 kDa, observing a certain degree of rupture during purification.

The chimeric gene was also cloned in the plasmid pQE, a vector that allows the expression of proteins with a fragment of 6 histidines at the extreme N-terminus. The resulting clone and the recombinant proteins are denominated pPQ and PQ respectively.

The level of expression of the protein in bacteria transformed with the pPQ plasmid and the purified proteins are shown in Figure number 4, referred to in particular with a D, with the protein PQ, purified by affinity chromatography in denaturising conditions is more stable that the recombinant protein pPQV represented in FIG. 4, in box D lane 2.

In order to evaluate the final product a series of materials were used, and obviously some techniques, as is described below.

Sera of VL obtained from dogs of different origins are used. The animals are evaluated clinically and analytically in the pertinent laboratory, generally in a Department of Parasitology, and all the positive sera are assayed for indirect immuno-fluoresence (IIF).

The presence of amastigotes of the parasites of these animals is confirmed by direct observation of the popliteal and pleescapular lymph nodes, and a second group of 33 sera of VL originating from other regions, were given a positive diagnosis in the ELISA against total protein extracts of the parasite and/or by IIF.

The sera of dogs affected by different diseases that were not VL are obtained from different origins. Within this group sera from the following infections are found:

*Mesocestoides* spp.

*Dyphylidium caninum*

*Uncinaria stenocephala*
*Toxocara canis*
*Dipetalonema dranunculoides*
*Demodex canis*
*Babesia canis*
*Ehrlichia cannis*
*Ricketsia ricketsiae.*

The rest of the sera were obtained from dogs that exhibited various clinical symptoms that were not related to any infective process, and the serum controls were obtained from fifteen carefully controlled healthy animals.

Purification of the recombinant proteins expressed by the clones pMAl-c2 is carried out by affinity chromatography on amylose columns, and the purification of the recombinant protein expressed by the clone pPQ was performed on Ni-NTA resin columns in denaturising conditions (Qiagen).

For analysing the proteins, electrophoresis on 10% polyacrimide gels in the presence of SDS was carried out under standard conditions. Immunological analysis of the proteins separated by electrophoresis was carried out on nitrocellulose membranes to which the proteins had been transferred. The transferred proteins were blocked with dried 5% skimmed milk in a PBS buffer with 0.5% Tween 20.

Figure 4C:
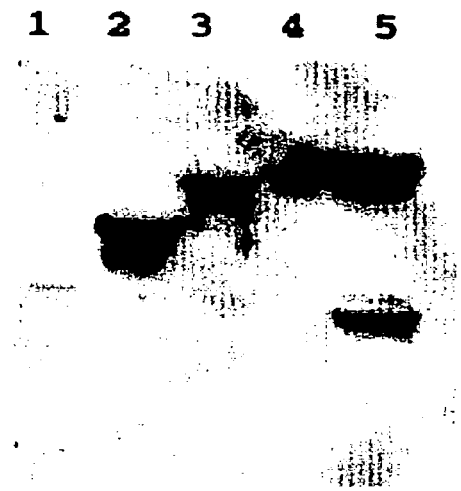
FIG. 4. Corresponds to the expression (A), purification in amylose columns (B) and the antigenicity (C: Western blot.
Figure 4D:
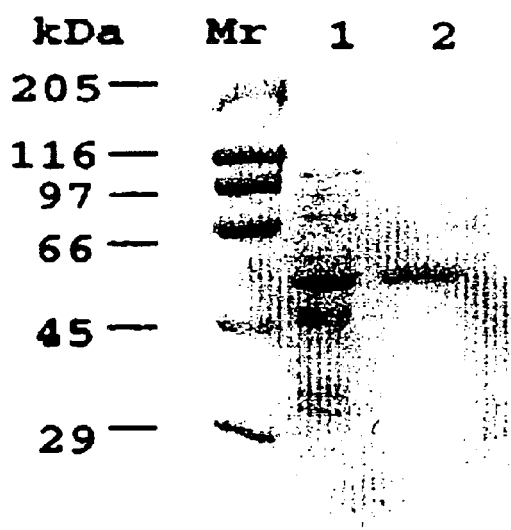
Figure 4E:
Figure 4F:
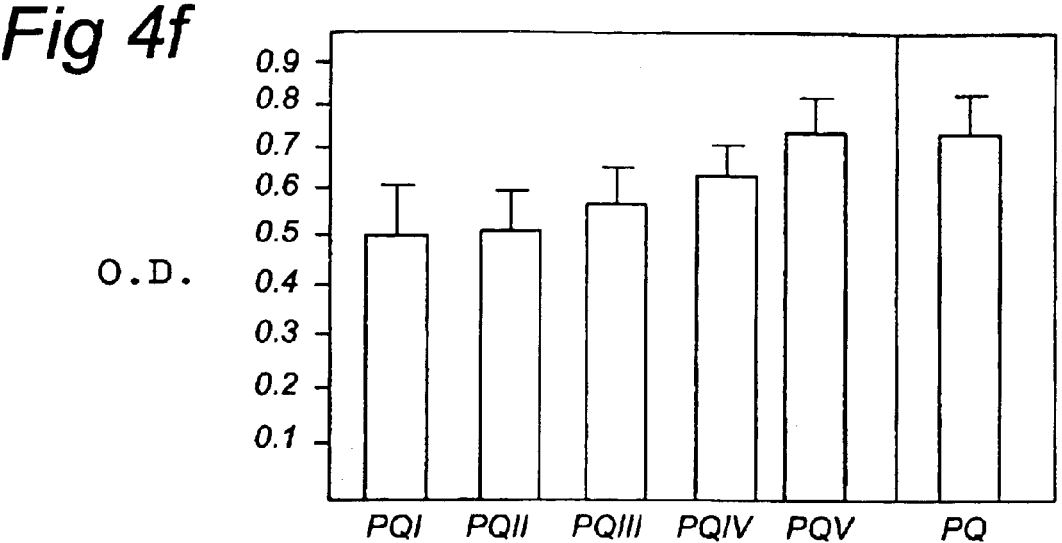

The filters were sequentially brought into contact with primary and secondary anti-serum in blocking solutions and an immuno-conjugate labelled with peroxidase was used as second antibody, visualising the specific binding by means of an ECL system. FIG. 4E shows a Western blot of protein PQ.

The Fast-ELISA was used instead of the classic ELISA, and the sensitisation of the antigen was carried out for 12 hours at room temperature.

The plates were sensitised with 100 $\mu$l of antigen whose concentration in all cases was 2 $\mu$g/ml.

After sensitising the wells the plates were incubated for 1 hour with blocking solution (0.5% powdered skimmed milk dissolved in PBS—0.5% Tween 20 and the sera were diluted three hundred fold in blocking solution).

The wells were incubated with serum for 2 hours at room temperature, and after exposure to the antibody the wells were washed with PBS-Tween 20.

Antibodies labelled with peroxidase were used as second antibodies at a dilution of 1:2000 and the colour of the reaction was developed using the substrate ortho-phenylenediamine, measuring the absorption at 450 nm.

In regard to evaluation of the final product, it should be pointed out that the antigenic properties were determined by means of the pertinent study of the reactivity of the VL canine sera against the chimeric protein and against each one of the intermediate products in a "Western blot" assay. All the intermediate products maintained their antigenicity as well as did the final pPQV product, throughout the whole of the cloning process (FIG. 4C).

It should also be pointed out that the recombinant protein expressed by the pPQ plasmid was recognised by the VL sera. With a view to analysing with greater precision the antigenic properties of the chimeric protein and the intermediate products, an analysis of the reactivity of a wide variety of VL canine sera was performed by means of a fast-ELISA against the recombinant proteins, as is shown in the section F of FIG. 4. It can be highlighted that the sensitivity of the different intermediate products of cloning increases after each addition step. It should also be pointed out that the protein pQI is recognised by most of the VL sera and the protein PQII equally by most of the sera. This proportion is greater for the protein PQIII and the proteins PQIV, PQV and PQ are recognised by practically all the sera.

According to what has been discussed above, the percentage of recognition shown by the sera was similar both in the case of assaying the chimeric proteins PQV and PQ, and of assaying a mixture of recombinant proteins rLiPO-Ct-Q, rLiP2a, rLiP2b and rLiH2A. It was seen that the antigenic properties of each one of the 5 selected antigenic regions are present in the PQ expression product, and therefore this product can be used for diagnosis instead of a mixture of the antigens expressed individually.

With a view to determining whether the chimeric protein can be used for canine VL serum diagnosis, and according to the pertinent analysis of a wide variety of canine sera against this protein, bearing in mind that according to the clinical characteristics of the animals, the canine sera have been classified into three groups. A first group consisted of sera from dogs with a real *L. infantum* infection. A second group was composed of sera of dogs that had various clinical symptoms without being infected with *Leishmania*, including dogs infected with parasites different to *Leishmania*, and that could exhibit clinical symptoms that could be confused with those observed during *Leishmaniosis*.

The third group was made up of control sera, originated from healthy dogs.

In FIG. 5 the average values of reactivity are shown for each group of sera, the reactivity of the VL sera reaching an average reactivity value of 0.8 (S.D.=0.4).

Within this group the reactivity of 12 sera was positive but less than 0.35, while the reactivity of 10 sera reaches values of between 0.35 and 0.5. It was observed that the reactivity of 23 sera varies between 0.5 and 1.0, with 14 sera showing a reactivity greater than 1.0.

The average absorption value of the sera of the second group, that is to say, the group infected with parasites different to *Leishmania* parasites, is 0.2 (S.D.=0.05) and the reactivity of the control sera, that is to say, the third group, is 0.1 (S.D.=0.003). Only two sera from group 2 showed reactivity between 0.35 and 0.40.

The data presented above indicate that the chimeric protein PQ in the FAST ELISA has a sensitivity of 80% for the VL diagnosis, if the cut-off value is defined as the average reactivity value of the sera of group 2 plus three S.D.'s (that is to say 0.35).

The sensitivity of the assayed group reaches 93%, if the cut-off value is defined by the reactivity values of the control group. The protein Q has a specificity of 96% for VL diagnosis, when the cut-off value is defined by the aforementioned sera of group 2. 100% specificity in the assay was reached when the reactivity values of healthy dogs were considered.

The process to be used is the following;

1.—The microtitre plates are covered with antibodies by incubated 100 $\mu$l of a solution that contains 1 $\mu$g/ml of antigen dissolved in a buffer PBS—0.5% Tween 20–5% skimmed milk (Buffer A).

The incubation is performed for 12 hours at room Temperature, and then the plates are washed three times with the same buffer containing no antigen. The dry antigenated plates could be maintained at room temperature.

2.—A first incubation of the wells was carried out with the serum of animal at a dilution of 1/200 in buffer A. The incubation lasts for 1 hour.

3.—The wells are washed with buffer A, as described in point 1, three times with a wash flask.

4.—They are incubated with a second antibody (IgG labelled with peroxide) diluted 1:2000 in buffer A, carrying out the incubation for 1 hour.

5.—The wells are washed once again with buffer A three times, as was indicated in the third section, that is to say with a wash flask.

6.—The reactivity is revealed using the substrate ortho-phenylenediamine and the absorption measured at 450 nm.

The protein used for the diagnosis extracted from the chimeric gene is identified, and the nucleotide sequence enconding said protein, are as follows:

(SEQ ID NO.1 and SEQ ID NO.2)

```
1                                                                45
ATG AGA GGA TCT CAC CAC CAC CAC CAC CAC ACG GAT CCG CAT GCG
Met Arg Gly Ser His His His His His His Thr Asp Pro His Ala
                 5                  10                      15

46                                                               90
AGC TCG AAC AAC AAC AAC AAT AAC AAT AAC AAC AAC CTC GGG ATC
Ser Ser Asn Asn Asn Asn Asn Asn Asn Asn Asn Asn Leu Gly Ile
                 20                 25                      30

91                                                               135
GAG GGA AGG CCT TTA GCT ACT CCT CGC AGC GCC AAG AAG GCC GTC
Glu Gly Arg Pro Leu Ala Thr Pro Arg Ser Ala Lys Lys Ala Val
                 35                 40                      45

136                                                              180
CGC AAG AGC GGC TCC AAG TCC GCG AAA TGT GGT CTG ATC TTC CCG
Arg Lys Ser Gly Ser Lys Ser Ala Lys Cys Gly Leu Ile Phe Pro
                 50                 55                      60

181                                                              225
GTG GGC CGC GTC GGC GGG ATG ATG CGC CGC GGC CAG TAC GCT CGC
Val Gly Arg Val Gly Gly Met Met Arg Arg Gly Gln Tyr Ala Arg
                 65                 70                      75

226                                                              270
CGC ATC GGT GCC TCT GGC GCC CCC AGG ATT TCA GAA TTC TCC GTG
Arg Ile Gly Ala Ser Gly Ala Pro Arg Ile Ser Glu Phe Ser Val
                 80                 85                      90

271                                                              315
AAG GCG GCC GCG CAG AGC GGG AAG AAG CGG TGC CGC CTG AAC CCG
Lys Ala Ala Ala Gln Ser Gly Lys Lys Arg Cys Arg Leu Asn Pro
                 95                 100                     105

316                                                              360
CGC ACC GTG ATG CTG GCC GCG CGC CAC GAC GAC GAC ATC GGC ACG
Arg Thr Val Met Leu Ala Ala Arg His Asp Asp Asp Ile Gly Thr
                 110                115                     120

361                                                              405
CTT CTG AAG AAC GTG ACC TTG TCT CAC AGC CCC GTT GTG CCG AAC
Leu Leu Lys Asn Val Thr Leu Ser His Ser Gly Val Val Pro Asn
                 125                130                     135

406                                                              450
ATC AGC AAG GCG ATG GCA AAG AAG AAC CCC CCC AAG AAG CCC AAG
Ile Ser Lys Ala Met Ala Lys Lys Gly Gly Lys Lys Gly Lys
                 140                145                     150

391                                                              495
GCG ACA CCG AGC GCG CCC GAA TTC GGA TCC TCT AGA CCC ATG TCC
Ala Thr Pro Ser Ala Pro Glu Phe Gly Ser Ser Arg Pro Met Ser
                 155                160                     165

496                                                              540
ACC AAG TAC CTC GCC GCG TAC GCT CTG CCC TCC CTG AGC AAG GCG
Thr Lys Tyr Leu Ala Ala Tyr Ala Leu Pro Ser Leu Ser Lys Ala
                 170                175                     180

541                                                              585
TCC CCG TCT CAG GCG GAC GTG GAG GCT ATC TGC AAG GCC GTC CAC
Ser Pro Ser Gln Ala Asp Val Glu Ala Ile Cys Lys Ala Val His
                 185                190                     195

596                                                              630
ATC GAC GTC GAC CAG GCC ACC CTC GCC TTT GTG ATG GAG AGC GTT
Ile Asp Val Asp Gln Ala Thr Leu Ala Phe Val Met Glu Ser Val
                 200                205                     210

641                                                              675
ACG GGA CGC GAC GTG GCC ACC CTG ATC GCG GAG GGC GCC GCG AAG
Thr Gly Arg Asp Val Ala Thr Leu Ile Ala Gln Gly Ala Ala Lys
                 215                220                     225

676                                                              720
ATG AGC GCG ATG CCG GCG GCC AGC TCT GGT GCC GCT GCT GGC GTC
Met Ser Ala Met Pro Ala Ala Ser Ser Gly Ala Ala Ala Gly Val
                 230                235                     240
```

-continued

```
721                                                           765
ACT GCT TCC GCT GCG GGT CAT GCG GCT CCC GCT CCC GCC GCC GCG
Gly Asp Ala Ala Pro Ala Ala Ala Ala Lys Lys Asp Gln Pro
                245                 250                 255

766                                                           810
AAG AAG GAC GAG CCC GAG GAG GAG CCC CAC CAC GAC ATG GGC CCC
Thr Ala Ser Ala Ala Glu Glu Glu Ala Asp Asp Asp Met Gly Pro
                260                 265                 270

811                                                           855
TCT AGA GTC GAC CCC ATG CAG TAC CTC GCC GCG TAC GCC CTC GTG
Ser Arg Val Asp Pro Met Gln Tyr Leu Ala Ala Tyr Ala Leu Val
                275                 280                 285

856                                                           900
GCG CTG TCT GGC AAG ACG CCG TCG AAG CCG GAC GTT CAG GCT GTC
Ala Leu Ser Gly Lys Thr Pro Ser Lys Ala ASP Val Gln Ala Val
                290                 295                 300

901                                                           945
CTG AAG GCC GCC GGC GTT GCC GTG GAT GCC TCC CGC GTG GAT GCC
Leu Lys Ala Ala Gly Val Ala Val Asp Ala Ser Arg Val Asp Ala
                305                 315                 315

946                                                           990
GTC TTC CAG GAG GTG GAG GGC AAG AGC TTC GAT GCG CTG GTG GCC
Val Phe Gln Glu Val Glu Gly Lys Ser Phe Asp Ala Leu Val Ala
                320                 325                 330

991                                                          1035
GAG GGC CGC ACG AAG CTG GTG GGC TCT GGC TCT GCC GCT CCT GCT
Glu Gly Arg Thr Lys Leu Val Gly Ser Gly Ser Ala Ala Pro Ala
                335                 340                 345

1036                                                         1080
GGC GCT GTC TCC ACT GCT GGT GCC GGC GCT GGC GCG GTG GCC GAG
Gly Ala Val Ser Thr Ala Gly Ala Gly Ala Gly Ala Val Ala Glu
                350                 355                 360

1081                                                         1125
GCG AAG AAG GAG GAG CCC GAG GAG GAG GCC GAT GAT GAC ATG
Ala Lys Lys Glu Glu Pro Glu Glu Glu Ala Asp Asp Asp Met
                365                 370                 375

1136                                                         1170
GGC CCC GTC GAC CTG CAG CCC GCC GCT GCC GCG CCG GCC GCC CCT
Gly Pro Val Asp Leu Gln Pro Ala Ala Ala Pro Ala Ala Pro
                380                 385                 390

1171                                                         1215
AGC GCC GCT GCC AAG GAG GAG CCG GAG GAG AGC GAC GAG GAC GAC
Ser Ala Ala Ala Lys Glu Glu Pro Glu Glu Ser Asp Glu Asp Asp
                395                 400                 405

TTC GGC ATG GGC GGT CTC TTC TAAGCGACTC GCCATCTCTT    1256
Phe Gly Met Gly Gly Leu Phe
                410     412

1258
AGCCTCCTTG TGGTGCGCTT GAGGTGCTCT CGCTCTGCTT CTCCTTGCAG 1306

1307
TGTTGGCTGA CTCTGGCGGG TATGTGCCGT CGCATTACAC CCACCTCTCC 1356

1357
CACCCCTTTG CCCTACGCGC TCGCATGCGC AATCCGTGAA TCATCGAGGG 1406

1407
AAGTCTCTCT GGGTGGCAGT GGGTAAGCTT 1436
```

It is not considered necessary to extend this description in order that someone skilled in the art can understand the scope of the invention and the advantages that it confers.

The materials, form, size and disposition of the elements are susceptible to change, provided it does not suppose a change in the essence of the invention.

The terms in which this disclosure has been written should always be considered as broad in nature and not limiting.

Vaccine Against *Leishmania*

BACKGROUND OF THE INVENTION

The protozoan parasites of the genus *Leishmania* are responsible for causing leishmaniasis, a symptomatically complex disease which essentially affects men and animals in tropical and subtropical regions. It is estimated that the number of new cases of human visceral leishmaniasis can reach the number of 500,000, there being a minimum of several tens of millions of persons affected. Additionally the number of cutaneous and mucocutaneous leishmaniasis can be of the order of 2.000.000 per year (Modabber., 1990). Although the persons at risk of contracting the different types of leishmaniasis can be estimated in about 350 million, the number of persons with real infection can be much higher, due to the fact that there are no clear estimations of the real cases of asymptomatic infections and because of the existence of cryptic infections. In fact, leishmaniasis can be considered within the global context as an infection/disease of endemic nature, situated between the $4^{th}$ and $5^{th}$ place in the ranking of parasitic diseases with world-wide repercussion.

Three main forms of leishmaniasis can be distinguished: cutaneous, mucocutaneous and visceral, the characteristics of which mostly depend upon the localisation of the parasite, the species to which it belongs and the clinical manifestations it produces. The species distributed along Asia and certain regions in the Mediterranean area bring about the presence of the cutaneous form, with localised ulceration which, in many cases, heal spontaneously. These manifestations are caused by *L. major* and *L. tropica. L. aethiopica* (Mediterranean, Asia, Africa) also induces the cutaneous form of leishmaniasis, although its manifestation is more diffuse. In America, the species *L. mexicana* produces the cutaneous form with a generalised localisation that does not usually heal spontaneously. The mucocutaneous form of the disease in humans is caused by *L. brasilieneis* and is characterised by the presence of cutaneous lesions in oronasal and pharyngeal regions, bringing about the destruction of the mucosae. In America, Europe, Africa and Asia, the most frequent form of leishmaniasis is the visceral form, caused by *L. chagasi, L. donovani* and *L. infantum*. This form of leishmaniasis is characterised by clinical symptoms associated to fever, anaemia and an intense hepato/splenomegalia, which is lethal if it is not treated suitably at the right time. In the advanced form of the disease, the host is incapable of developing an effective immune response. All of these forms of leishmaniasis are also detected in canids and some rodents which, in fact, constitute the main reservoirs of the parasite. The health problem generated by *L. infantum* in the Mediterranean basin is serious because there is a high incidence of the infection/disease in dogs, and the vector insect is very extended. It is calculated that between 7% and 20% of all canids are infected by *Leishmania*, reaching 30%, in some areas of Spain where it is endemic. This fact constitutes a serious veterinary problem which additionally increases the risk of contagion, fundamentally by immunodepressed persons. In Europe, there are some 11 million dogs at risk of infection by *Leishmania*.

*L. infantum*, like the rest of the species in the genus has a dimorphic biological cycle. The intermediate hosts are insects of the Psychodidae family, genus *Phlebotomus*. In the Mediterranean area of Europe, it has been demonstrated that the species *P. arias* and *P. perniciosus* are the main vectors, although the vectors *P. papatosi, P. longicuspi* and *P. sergenti* are also present. When the parasite is ingested by the vector together with the blood of a vertebrate host, it places itself in the gut in an extracellular form, it transforms into a promastigote and it divides. The infective forms migrate towards the pharynx and the proboscis, from where they will be inoculated into a new vertebrate host. The promastigotes are characterised in that they have a flagellum and an elongated shape of some 15 to 20 μm in length, with a rounded posterior end and a sharp anterior end. The nucleus is situated in central position and the kinetoplast at the anterior end. In culture media, the parasites exhibit a certain degree of morphological variability. After the inoculation of the promastigotes in the skin of the vertebrate host, the establishment, or not, of the infection depends essentially upon two factors: the existence of a suitable cell population—macrophages—and other cells of the phagocytic mononuclear system, and the ability of the parasite to survive and multiply itself in the interior of these cells.

The first step in the penetration of *Leishmania* into macrophages is the approximation and adherence to the plasma membrane of the target cell. In vitro studies seem to indicate that there is no direct chemotactic attraction of the promastigotes over the macrophages. Within the environment of tissues, free promastigotes activate complement by the alternative pathway, bringing about the formation of a concentration gradient of fraction C5a, which attracts macrophages and other inflammatory cells towards the site of inoculation. Once the promastigote is within a parasitophorous vacuole, the lysosomes fuse to it forming a phagolysosome. In infections caused by other micro-organisms, the phagolysosome is the organelle responsible for the lysis and elimination by means of several mechanisms such as the production of toxic oxygen radicals, by an oxidative metabolic process, the action of hydrolytic lysosomal enzymes, cationic proteins and low pH. The survival of the parasite in the phagolysosome is a function of its ability to resist and avoid said mechanisms.

The existence of an immune response against parasitisation by *Leishmania* which is both humoral and cellular was discovered from the first moments in which the disease was studied, and has been revised in numerous occasions. The type of humoral response depends upon the form of leishmaniasis. In the cutaneous form, the humoral response is very weak, whereas in the visceral type a high antibody response is observed. In the cutaneous affections there is a remarkable cell-mediated response, detectable both in vivo by means of delayed type hypersensitivity tests (DTH), as well as in vitro by means of lymphoblastic transformation tests and macrophage migration inhibition tests. In these cases the titre of serum antibodies is normally low and directly related to the seriousness of the process. Once the amastigotes are within the macrophages, the resolution of the infection depends essentially upon the cell-mediated immune mechanisms. The cellular response is determined by the joint action of macrophages, B cells, several sub-populations of T-cells, and the different lymphokines secreted by all of them. The parasitised macrophage processes the *Leishmania antigens* and expresses them on its surface by a process mediated by the class II Major Histocompatibility Complex (MHC-II), Additionally, the macrophage secretes IL-1, which acts as a second activating signal for the T-lymphocyte. In humans, visceral leishmaniasis or kala-azar is characterised by a weakened or absent cellular response, detectable both by the absence of delayed hypersensitivity (DTH) and by cell proliferation methods. Absence of proliferation of T-cells is detected even in the presence of mitogens such as concanavelin A or phytohaemagglutinin and inhibition in the production of IL-2 by stimulated T-cells.

In mice, the population of T-lymphocytes (CD4 phenotype) is heterogeneous and can be divided into at least two sub-populations according to the lymphokines they produce. These cells are essential in the development of protective immunity against cutaneous leishmaniasis (sub-population Th-1) and are at the same time involved in the suppression of the protective immune response (sub-population Th-2), T cells induced in resistant mice C57BL/6 or cured BALB/c mice are predominantly of the Th-1 type, whereas the cells in uncured BALB/c mice are of the Th-2 type. In general, the lymphokines secreted by these cells favour the development of the cell line which produces them and has an antagonic effect on the development of the other sub-population. Thus, IL-4 and IL-10 produced by Th-2 cells contribute to the progression of the infection, favouring the development of this line. Additionally, they can act directly on the macrophage, not permitting its activation. However, in mice susceptible of infection by *Leishmania*, deficient in the gene which encodes IL-4, contradictory results have been obtained. In some cases it has been observed that the absence of this cytokine redirects the response and increases the resistance to the infection whereas in others no differences are observed in the level of infection of the mice. In genetically resistant mice it has been observed that the absence of expression of the genes of IFN-$\gamma$ or its receptor, CD40 or the ligand of CD40, increases the susceptibility to the infection. The interaction of CD40 and its ligand is necessary for the production of the cytokine TFN-$\gamma$ necessary to direct the response towards Th-1. Mice with a resistant genetic base, which develop a Th-1 type response, become susceptible if they are deficient in the expression of IL-12, developing a Th-2 type response. Recent data suggests that the production of IL-12 is important to direct the response towards Th-1, and that the absence of IL-4 can avoid the Th-2 response.

There are a large number of *Leishmania* proteins which have an antigenic character essentially characterized by "Western Blot" methods. In the serum of patients and dogs infected by *Leishmania* it has been possible to detect the presence of antibodies against membrane proteins such as gp63, gp 46, PSA and KPM-11. Additionally several antigens of cytoplasmatic intracellular localisation have been characterised such as; Hsp70; Hsp83; LIP2a, LIP2b, LILIP0, H2A, H3 and a protein related to kinesin, K39 of *L. chagasi*. The reactivity of the antibodies, which recognise conserved proteins present in the serum of dogs infected by *L. infantum* is directed towards the least conserved areas of these proteins. Some of the membrane proteins are very antigenic in natural infections. In all the cases of natural infection there is a great restriction in the humoral response against the proteins because the antibodies developed during the infective process recognise very restricted areas of the same. The levels of IgG normally correspond to the intensity of the infection reflect the degree and the duration of antigenic stimulation determined by the parasitic load. A *Leishmania* antigen homologous to the type C kinase receptors (LACK) has recently been described which produces an early response of the Th-2 type. In mice transgenic for the LACK antigen and with a genetic background susceptible to the infection, the induction of tolerance to this antigen protects against the infection by *Leishmania* major. The anti-*Leishmania* antibodies can destroy the promastigotes in vitro in the presence of complement, promote phagocytosis and induce the adherence of several particles to the surface of promastigotes and amastigotes.

The pathologic reaction seems to go in parallel with the density of parasitised macrophages. In visceral leishmaniasis the macrophages generally distribute themselves in a diffuse manner throughout the different organic tissues. The type of inflammation is is constituted by an important cellular infiltrate with a predominance of lymphocytes and plamatic cells together with hyperplasia of phagocytic cells. The inflammation brings about alterations in the physiology of the affected organs producing serious systemic alterations. In some occasions local granulomatous inflammation occurs, with appearance of granulomae and microgranulomae in the different organs. These granulomae are constituted by macrophages and histiocytes (affected by parasites or not) surrounded by plasmatic cells and lymphocytes and, in some cases, by fibroblasts. This inflammatory process is accompanied by an organic reaction with the appearance of characteristic lesions in the affected organs. Some authors have found deposits of amyloid substance in virtually the totality of the organs. Some authors have formulated the hypothesis that the damages produced by the disease are not directly attributable to the aethiologic agent but to the organic reaction triggered.

Vaccine Against *Leishmania*

The intense immunity which follows the recovery from cutaneous leishmaniasis has given a great impulse to the development of prophylactic vaccines against this disease. This immunity is derived from the induction of a T response which has associated to it the production of inflammatory cytokines which activate macrophages and destroy the parasites. The immunological memory in the cases of infection is probably maintained by the persistent presence of the parasite in the host in a process known as concomitant immunity.

The first studies regarding vaccination against *Leishmania* in the decade of the 40's used live parasites as immunogens. These studies led to the production of vaccines which produced significant protection against subsequent re-infection. However, the knowledge of the possibility that live organisms could produce real infections led to such vaccination programmes not to take place for very long and, on the contrary, interest focused upon vaccines based upon dead parasites. These studies provided the first evidence on the possibility of producing effective vaccines by inoculation of parasites.

The clinical trials which used immunisation with dead *Leishmania* promastigotes also began in the decade of the 40's. These vaccines yielded remarkable successes as a certain degree of protection was observed, which could oscillate between 0 and 82% depending on the population. These vaccines had a smaller effect than live parasite vaccines. The isolation of avirulent clones of *L. major* which protect mice against infection has also demonstrated that an attenuated vaccine is possible. However, the ignorance of the mutations which lead to the loss of virulence and the risk of production of virulent revertants make this type of vaccination currently unacceptable.

Recently there has been an important progress towards the identification of molecularly defined candidate vaccines, such as gp63, gp46/M2, the surface antigen related to the latter antigen known as PSA-2 and the proteins dp72 and gp70–2, the LACK protein and Kmp11. Specifically, the T epitopes present in protein gp63 have been identified, resulting in that only some of them are capable of inducing a T response, both of Th-1 as of Th-2. These antigens induce significant protection in model animals when they are administered with adjuvants. Protein PSA-2 of *Leishmania* is capable of protecting against infection by L, major by inducing a Th-1 response. To evaluate the mechanism of protection of this protein as a vaccine against *Leishmania* in humans, its ability to induce T-cell proliferation was studied, in patients which had suffered leishmaniasis and had recovered from it. It was observed that the protein is capable of bringing about a strong proliferation of the T-cells of these individuals, but not of controls with no prior history of infection. The response was of the Th-1 type, as was demonstrated by the cytokine induction pattern.

Sub-unit vaccines have focused strongly on protein antigens because they are easy to identify, isolate and clone. However, it is necessary to take into account that not all potential vaccine molecules have to be proteins. In fact, lipophosphoglycan (LPG) plays an essential role in the establishment of infection. Vaccination with LPG can protect against infection with *L. major*. In spite of the existence of a dogma which states that T-cells do not recognise non-proteinaceous antigens, the LPG molecule seems to be presented to T-cells by Langerhans cells of the skin. Additionally, there is evidence which has demonstrated that microbial glycolipids and other non-proteinaceous molecules can recognise T-cells when they are presented via the CD-1 route. Although there is no clear evidence that protein KMP11 associated to LPG induces a protective response, it has been proved that the proteinaceous fraction associated to LPG is capable of inducing a T response and IFN-γ, whereas the LPG fraction without protein is not.

It is normally accepted that sub-unit vaccines although protective, only induce a short term immunity. This problem may not be important in endemic areas, where the individuals can be periodically boosted by cause of natural infections. A major problem in the use of sub-units may arise from the fact that there may not be a response to a single antigen in a genetically diverse population. A cocktail of antigens containing B and T inducers may overcome this drawback. It has recently been published that an extract of membrane proteins of *Leishmania infantum*, when injected intraperitoneally, is capable of conferring protection against the virulent promastigote forms of this parasite, and that this protection is greater when the proteins are encapsulated in positively charged liposomes. Adjuvanticity and protective immunity were elicited by *Leishmania donovani* antigens encapsulated in positively charged liposomes.

Vaccination with nucleic acids carrying genes which encode *Leishmania* proteins involves the administration of genetic material of the parasite to the host. This DNA is taken up by the cells and is introduced into the nucleus where it is transcribed and subsequently translated in the cytoplasm. The advantage of this type of vaccination is that it is possible to direct the immune response by means of the MHC-I or the MHC-II route. The antigens produced intracellularly are processed in the cell and the peptides generated are presented on the cell surface in association with MHC-I molecules. The consequence would be that these molecules would give rise to the induction of cytotoxic T-cells. The antigens produced in an extracellular environment would be specially taken up by specialised antigen-presenting cells, processed and presented on their surface bound to MHC-II molecules, resulting in the induction and activation of CD4+ cells which secrete cytokines which regulate the effector mechanisms of other cells of the immune system.

The first DNA vector to be administered as a vaccine contained the gp63 gene. Also, the PSA-2 gene has been introduced into a plasmid and it has been observed that it generates a Th-1 response and induction of protection. Vaccination with DNA plasmids which contain Ag-2 induce a Th-1 response and protect against infection with *L. major*, while Ag-2 in stimulators immune complexes elicits a combined Th-1 and Th-2 response and does not protect despite the fact that IFN-γ is induced. Equally, the gene encoding the LACK protein has been administered subcutaneously to BALB/c mice, in an expression vector which expresses the protein under the control of the cytomegalovirus promoter, and protection against infection with *L. major* has been observed. In almost all cases in which DNA has been administered, the route has been intramuscular, although intradermal injection of particulate DNA must also be explored, as it requires a smaller amount of DNA. Other immunisation systems use vectors such as *Salmonella*, BCG or *Vaccinia virus*. It is interesting to remark that the inclusion of the gp63 gene in BCG is capable of inducing protection against *L. major*.

The gene which encodes protein gp63 has also been introduced into gene delta araC under the control of the rac promotor in an attenuated *Salmonella typhimurium*. Oral administration of $1 \times 10^9$ colonies of the transformed bacterium induces a T response within the scope of both Th-1 and of cytotoxic cells against mastocytoma cells which express gp63. Protein gp63 in the form of gp63-ISCOMs complex induces protection in mice, evidenced by the reduction in inflammation and suppression of lesions. In serum, there are antibodies of the IgG2a type and, additionally, it is possible to observe a Th-1 response by induction of IL-2, IFN-γ and IL-10. No DTH response was observed. *Salmonella typhi* Nramp 1 transformed with gp63 elicits a Th-1 response with induction of IL-2 and IFN-γ, and a strong resolution of the lesions is detected. A protein of *L. pifanoi* known as P-4 induces significant protection against infection by *Leishmania*. Recent studies in humans with cutaneous leishmaniasis indicate that this protein or the peptides derived from it are capable of making T cells proliferate. There is no induction of IL-4, whereas IFN-γ is induced. Aro-A and aro-D mutants of *Salmonella typhi* transformed with IL-2, IFN-γ and TNF-α administered orally may serve as therapeutic Systems against infection by *L. major*. It is interesting to observe that in these patients there is a greater induction of iNOS. The gp&3 gene has also been cloned in Aro-A and Aro-D mutants, and it has been observed that after oral administration, the protein encoded is capable of inducing significant protection against infection with *L. major*. This same protein is capable of inducing protection when it is administered fused to several promoters in specific varieties (GID105 and GID106) of Salmonella.

An artificial protein denominated Q has recently been described by our group, which is composed of several antigenic fragments from 4 proteins of *Leishmania infantum* (more specifically, Lip2a, Lip2b, P0 and H2A), which, after being used as antigen, has proven to have an important value for the diagnosis of canine leishmaniasis, with a 93% sensitivity and a 100% specificity when compared with sera of control animals which are not infected. Equally, our group has demonstrated that protein hsp70 of *Leishmania infantum* is an important target of the immune response in infections caused by infection with this parasite.

With the object of exploring the possibility that protein Q may be used to design protection systems against infection by *Leishmania infantum*, both on its own as in combination with Hsp70, three series of experiments were designed using the hamster as a model. An experiment was designed to check whether immunisation with Protein Q protected the animals against infection on the short term, another to check whether immunisation protected them on the long term and the third was to check this protective effect after immunisation with the two proteins together. It was thereafter observed both from the short term analysis as well as from the long term analysis, that protein Q was capable of eliciting an immune response which reduces the parasitic load both in the Liver and in the Spleen after infection by *Leishmania infantum* in most of the immunised animals, and that immunisation with the proteins Q+Hsp70 also induced a significant response against both proteins and lead to a significant reduction of the parasitic load in most of the immunized animals.

EXAMPLE 1

Immunisation with Protein Q 4 animals were immunised with 5 micrograms of protein Q dissolved in 40 microliters of Freund's adjuvant, and another 4 animals were immunised with the same amount of adjuvant emulsified with 40 microliters of PBS saline solution without the protein. In the first immunisation, Freund's complete adjuvant was employed combined with the protein, while in the two subsequent immunisations, incomplete Freund's adjuvant was used mixed with the protein in the same proportion of protein/adjuvant. Three intraperitoneal immunizations were carried out at 15 day intervals. Starting from the second week after each immunisation and throughout the whole period of immunisation, blood samples were extracted to measure the humoral response against protein Q in ELISA assays. It was observed that already in the second week after the first immunisation there is a positive IgG response against protein Q, and that this response was high after the second week after infection, and increased with time of immunisation reaching titres of 1/100.000. Equally, it was observed that immune response against protein Q was not modified significantly after the infection with the parasite Table 4.

Fifteen days after the third immunisation, the animals were infected with a dose of $10^5$ promastigote parasites, differentiated from infective amastigotes originating from an infected hamster. It had been previously checked that the inoculum was capable of inducing a strong parasitemia together with the disease four months after having administered the parasites, in 100% of the animals infected. Table 1 indicates the level of parasitemia per mg of tissue both in liver and in the spleen of the control and the vaccinated animals. It is possible to observe that in all of the vaccinated animals the parasitic load in the liver decreases with respect to the controls, and that this happens in a very significant manner in 75% of them. When the parasitic load in the spleen is examined, it possible to observe that also in 75% of the animals this load was significantly lower than that of the controls, the RPL reaching 83%–86%. The animal in which the RPL was 20% in the liver, had a 48% one in the spleen.

TABLE 1

Parasitic load in the liver and spleen of hamsters vaccinated with protein Q via the intraperitoneal route. After four weeks of infection, the parasitic load was measured by the method of limit dilutions (short term). The parasitic load is expressed as parasites per milligram of tissue. RPL = reduction in parasitic load in %.

| | Hamster immunized with the Q protein | | | |
|---|---|---|---|---|
| Hamster | Liver | (RPL) | Spleen | (RPL) |
| 1 | 4 ± 1 | (71%) | 49 ± 3 | (83%) |
| 2 | 3 ± 2 | (78%) | 39 ± 2 | (86%) |
| 3 | 5 ± 1 | (64%) | 50 ± 4 | (83%) |
| 4 | 11 ± 3 | (20%) | 153 ± 19 | (48%) |

The numbers represent the mean of three determinations

TABLE 1-continued

Parasitic load in the liver and spleen of hamsters vaccinated with protein Q via the intraperitoneal route. After four weeks of infection, the parasitic load was measured by the method of limit dilutions (short term). The parasitic load is expressed as parasites per milligram of tissue. RPL = reduction in parasitic load in %.

| Controls | | |
|---|---|---|
| 4 hamsters | 14 ± 5 | 295 ± 30 |

The number represent the mean of the 4 animals

EXAMPLE 2

In order to verify the effect of vaccination with protein Q on the reduction of the parasitic load on the long term, using another route of inoculation, 4 animals were injected subcutaneously with 5 micrograms of protein Q dissolved in 40 microliters of PBS and mixed with 40 microliters of Freund's adjuvant. In the first immunisation, Freund's complete adjuvant was employed, while in the two subsequent ones, incomplete Freund's adjuvant was used as indicated above. Vaccination was administered in three doses spaced at 15 day intervals. Fifteen days after the third immunisation they were administered an inoculum of $10^5$ infective parasites. During all of the immunisation period and throughout the whole of the infection (five months) blood was extracted to determine the kind of humoral response against protein Q and against the total proteins of the parasite. Table 5 shows that already after the second week of immunisation, the response against protein Q was positive, as in the previous case, in three of the mice, and that the response against the protein was very high after two weeks of the first immunisation. The response kept on being very high after the remaining immunisations, reaching a titre of 1/75.000 on the week following the third immunisation. In one of the animals the response against protein Q was slower in relation to time, although the response reached the level of that in the other animals by the end of the experiment. Consequently, from the data derived both from example 1 and from example 2, it is possible to conclude that the degree of the immune response against the protein, by both routes, intraperitoneal and subcutaneous, is very rapid, although the response via the intraperitoneal route attained higher titres in the same times (1/75.000 versus 1/30.000). Table 5 indicates the response against protein Q in the control animals. It is possible to observe that reactivity against this protein is detected on the 12–14 th week after infection, which is when the first symptoms attributable to a potential leishmaniasis begin to be detected in the animals infected. Table 2, shows the levels of parasitemia in the liver and spleen of the control and vaccinated animals. It can be seen that 50% of the animals were protected at the level of the liver, in the sense that the reduction in the level of parasitemia was very high (87–89%). One of the animals was not protected, whereas in another of the animals the reduction of the parasitic load was of 22%. On the contrary, the reduction of the parasitic load was of 98–99% in 100% of the animals at the level of the spleen.

TABLE 2

Parasitic load in the liver and spleen of hamsters vaccinated with protein Q by the subcutaneous route. After 20 weeks of infection, the parasitic load was measured by the method of limit dilutions (long term). The parasitic load is expressed as parasites per milligram of tissue. RPL = reduction in parasitic load in %.

Hamsters immunized with the Q protein

| Hamster | Liver | (RPL) | Spleen | (RPL) |
|---|---|---|---|---|
| 1 | $1.4 \times 10^6$ | (22%) | $1.0 \times 10^7$ | (98%) |
| 2 | $2.0 \times 10^5$ | (89%) | $4.9 \times 10^9$ | (99.9%) |
| 3 | $2.4 \times 10^5$ | (87%) | $3.3 \times 10^5$ | (99.9%) |
| 4 | $2.4 \times 10^6$ | (0%) | $6.3 \times 10^5$ | (99.9%) |

The number represent the mean of three determinations

Controls

| 4 hamsters. | $1.8 \times 10^6 \pm 12 \times 10^5$ | $5.2 \times 10^8 \pm 2.6 \times 10^7$ |

The numbers represent the mean of the parasitic load of the 4 animals

With the object of testing if protein Q could be used to design protection systems in formulations which contained protein LiHsp70 of *Leishmania infantum*, an experiment was carried out in Balb/c mice. It was observed that after immunisation, the parasitic load both in the liver as in the spleen was reduced significantly, being in some of the animals, four orders of magnitude lower.

EXAMPLE 3

Immunisations with Protein Q+Protein Hsp70 in Freund's Adjuvant.

Each one of 4 hamsters were injected intraperitoneally with 5 micrograms of protein Q and 5 micrograms of protein LiHsp70 dissolved in 40 microliters of PBS and emulsified in 40 microliters of Freund's adjuvant. In the first immunisation, Freund's complete adjuvant was employed, while in the two subsequent ones, incomplete Freund's adjuvant was used as indicated above. Vaccination was administered in three doses spaced at 15 day intervals.

Fifteen days after the third immunisation they were administered an inoculum of $10^6$ infective parasites via the intracardiac route and were sacrificed at week 22. Every two weeks, for all of the immunisation period and throughout the whole of the infection, blood was extracted from them to determine the degree of humoral response against protein Q and against protein LiHsp70.

The relative parasitic load between the mice immunized with the Q protein plus LiHsp70 is shown in Table 3. It was observed that all the animals were highly protected and in some of them, in the spleen, the reduction was close to two-three orders of magnitude.

TABLE 3

Relative parasitic load of Balb/c mice immunized with the Q plus LiHsp70 protein after 4 month of infection.

| Mice immunized with the protein Q and LiHsp70 | | | | |
|---|---|---|---|---|
| Mouse | Liver | (RPL) | Spleen | (RPL) |
| 1 | $1.5 \times 10^3$ | (97%) | $1.5 \times 10^4$ | (99%) |
| 2 | $0.9 \times 10^3$ | (98%) | $1.4 \times 10^3$ | (99%) |
| 3 | $2.0 \times 10^4$ | (60%) | $5.6 \times 10^4$ | (99%) |
| 4 | $0.8 \times 10^4$ | (84%) | $1.2 \times 10^5$ | (96%) |

The numbers represent the mean of three determinations.

TABLE 3-continued

Relative parasitic load of Balb/c mice immunized with the Q plus LiHsp70 protein after 4 month of infection.

| Controls | | |
|---|---|---|
| 4 mice | $5.1 \times 10^4 \pm 2 \times 10^3$ | $3.2 \times 10^6 \pm 8 \times 10^4$ |

The numbers represent the mean of the parasitic load of the 4 animals.

Tables 4 and 5 shows that all the animals from Examples 1 and 2 respond immunologically to protein Q, and that starting from the second week after immunisation the response against protein Q was high and this response increased after the second immunisation (week 4). Table 6 shows that the response against protein LiHsp70 throughout the whole time of the experiment was also positive, although lower than the response in Example 3 against protein Q.

Tables 4 and 5. Show the immune response in 4 hamsters injected intraperitoneally with 5 micrograms of protein Q (TABLE 4—Example 1, short term) and the immune response in 4 hamsters injected subcutaneously with 5 micrograms of protein Q (TABLE 5—Example 2, long term).

TABLE 4

Example 1, short term

| Week | Mouse 1 | Mouse 2 | Mouse 3 | Mouse 4 |
|---|---|---|---|---|
| Mice Immunized with the Q protein (Short term) Immune response against the Q protein | | | | |
| 2 | 0.8 | 0.2 | 0.3 | 0.6 |
| 4 | 1.9 | 2.3 | 1.1 | 2.1 |
| 6 | 3 | 3 | 2.4 | 2.9 |
| Infected | | | | |
| 8 | 3 | 3 | 2.9 | 3 |
| 10 | 3 | 3 | 3 | 3 |
| The sera (diluted 1/200) showing an optical density of 3 have a titre higher than 1/45,000. | | | | |
| Control mice Immune response against the Q protein (Short term). | | | | |
| 2 | 0 | 0 | 0 | 0 |
| 4 | 0 | 0 | 0 | 0 |
| 6 | 0 | 0 | 0 | 0 |
| 8 | 0 | 0 | 0 | 0 |
| 10 | 0 | 0 | 0 | 0 |

The sera were diluted 1/200

TABLE 5

Example 2, long term

| Week | Mouse 1 | Mouse 2 | Mouse 3 | Mouse 4 |
|---|---|---|---|---|
| Mice immunized with the Q protein (Long term). Immune response against the Q protein | | | | |
| 2 | 1.8 | 1.3 | 1.9 | 0.4 |
| 4 | 2.1 | 1.8 | 2.2 | 0.7 |
| 6 | 2.5 | 2.7 | 2.5 | 0.5 |
| 8 | 2.8 | 2.2 | 2.2 | 0.8 |
| 10 | 3 | 2.9 | 2.5 | 0.7 |
| 12 | 3 | 3 | 3 | 0.9 |
| 14 | 3 | 3 | 3 | 1 |
| 16 | 3 | 3 | 2.9 | 1.5 |
| 18 | 3 | 3 | 3 | 1.7 |
| 20 | 3 | 3 | 3 | 2.2 |
| 22 | 3 | 3 | 3 | 2.6 |
| 24 | 3 | 3 | 3 | 3 |
| 26 | 3 | 3 | 3 | 3 |

The sera (diluted 1/200) showing an optical density of 3 have a titre higher than 1/45,000.

TABLE 5-continued

Example 2, long term

| Week | Mouse 1 | Mouse 2 | Mouse 3 | Mouse 4 |
|---|---|---|---|---|
| Control mice | | | | |
| Immune response against the Q protein (Long term). | | | | |
| 2 | 0 | 0 | 0 | 0 |
| 4 | 0 | 0 | 0 | 0 |
| 6 | 0 | 0 | 0 | 0 |
| 8 | 0 | 0 | 0 | 0 |
| 10 | 0 | 0 | 0 | 0 |
| 12 | 0.2 | 0.1 | 0.3 | 0.1 |
| 14 | 0.3 | 0.5 | 0.4 | 0.2 |
| 16 | 0.4 | 0.5 | 0.7 | 0.3 |
| 18 | 0.9 | 1.1 | 1.7 | 0.6 |
| 20 | 1.1 | 1.3 | 1.5 | 0.8 |
| 22 | 2.5 | 2.3 | 2.7 | 1.9 |
| 24 | 2.3 | 2.1 | 1.8 | 2.2 |
| 26 | 1.9 | 2.2 | 2.3 | 2.7 |

The sera were diluted 1/200

TABLE 6

Shows the immune response in 4 hamsters injected intraperitoneally with 5 micrograms of protein Q plus 5 micrograms of protein LiHSP 70 (Example 3, long term).

| Week | Mouse 1 | Mouse 2 | Mouse 3 | Mouse 4 |
|---|---|---|---|---|
| Mice immunized with the Q protein + Hsp70 | | | | |
| Immune response against the Q protein | | | | |
| 2 | 0.4 | 0.6 | 0.5 | 0.4 |
| 4 | 1.6 | 1.1 | 1.6 | 1.7 |
| 6 | 3 | 2 | 1.9 | 1.9 |
| 8 | 3 | 2.4 | 2.6 | 2.5 |
| 10 | 3. | 2.9 | 3 | 2.9 |
| 12 | 2.7 | 2.9 | 2.9 | 2.9 |
| 14 | 2.5 | 2.6 | 2.9 | 2.7 |
| 16 | 2.6 | 2.5 | 2.5 | 2.4 |
| 18 | 2.8 | 2.7 | 2.7 | 2.5 |
| 20 | 2.5 | 2.8 | 2.4 | 2.7 |
| 22 | 2.5 | 2.4 | 2.8 | 2.9 |

The sera were diluted 1/800

| Week | Mouse 1 | Mouse 2 | Mouse 3 | Mouse 4 |
|---|---|---|---|---|
| Control mice | | | | |
| Immune response against the Q protein | | | | |
| 2 | 0 | 0 | 0 | 0 |
| 4 | 0 | 0 | 0 | 0 |
| 6 | 0 | 0 | 0 | 0 |
| 8 | 0 | 0 | 0 | 0 |
| 10 | 0 | 0 | 0 | 0 |
| 12 | 0 | 0.1 | 0.2 | 0.1 |
| 14 | 0.3 | 0.4 | 0.2 | 0.5 |
| 16 | 0.5 | 0.6 | 0.7 | 0.7 |
| 18 | 0.8 | 1.4 | 1.1 | 1.5 |
| 20 | 1.8 | 1.6 | 1.8 | 2.2 |

The sera were diluted 1/200

| Week | Mouse 1 | Mouse 2 | Mouse 3 | Mouse 4 |
|---|---|---|---|---|
| Mice immunized with the Q protein + Hsp70 | | | | |
| Immune response against the Hsp70 protein | | | | |
| 2 | 0.1 | 0.2 | 0.1 | 0.4 |
| 4 | 0.4 | 0.6 | 0.3 | 0.5 |
| 6 | 0.8 | 0.7 | 0.4 | 0.3 |
| 8 | 0.7 | 1.1 | 1.2 | 0.5 |
| 10 | 1.2 | 1.4 | 1.5 | 0.8 |
| 12 | 1.9 | 1.9 | 2 | 1.2 |
| 14 | 2 | 1.8 | 2.2 | 1.7 |
| 16 | 1.9 | 2 | 2.2 | 1.9 |
| 18 | 2. | 2.1 | 2 | 2 |
| 20 | 2 | 2.1 | 2.2 | 1.9 |
| 22 | 2.4 | 2.3 | 2.1 | 1.9 |

The sera were diluted 1/800

TABLE 6-continued

Shows the immune response in 4 hamsters injected intraperitoneally with 5 micrograms of protein Q plus 5 micrograms of protein LiHSP 70 (Example 3, long term).

| Week | Mouse 1 | Mouse 2 | Mouse 3 | Mouse 4 |
|---|---|---|---|---|
| Control mice | | | | |
| Immune response against the Hsp70 protein | | | | |
| 2 | 0 | 0 | 0 | 0 |
| 4 | 0 | 0 | 0 | 0 |
| 6 | 0 | 0 | 0 | 0 |
| 8 | 0 | 0 | 0 | 0 |
| 10 | 0 | 0 | 0 | 0 |
| 12 | 0.1 | 0 | 0.3 | 0 |
| 14 | 0.3 | 0.2 | 0.5 | 0.4 |
| 16 | 0.5 | 0.6 | 0.6 | 0.3 |
| 18 | 0.7 | 0.6 | 0.7 | 0.5 |
| 20 | 1 | 0.8 | 0.5 | 1.2 |
| 22 | 1.7 | 1.4 | 0.8 | 1.1 |

The sera were diluted 1/200

| Week | Mouse 1 | Mouse 2 | Mouse 3 | Mouse 4 |
|---|---|---|---|---|
| Mice immunized with the Q protein + Hsp70 | | | | |
| Immune response against the Hsp70 protein | | | | |
| 2 | 0.1 | 0.2 | 0.1 | 0.4 |
| 4 | 0.4 | 0.6 | 0.3 | 0.5 |
| 6 | 0.8 | 0.7 | 0.4 | 0.3 |
| 8 | 0.7 | 1.1 | 1.2 | 0.5 |
| 10 | 1.2 | 1.4 | 1.5 | 0.8 |
| 12 | 1.9 | 1.9 | 2 | 1.2 |
| 14 | 2 | 1.8 | 2.2 | 1.7 |
| 16 | 1.9 | 2 | 2.2 | 1.9 |
| 18 | 2. | 2.1 | 2 | 2 |
| 20 | 2 | 2.1 | 2.2 | 1.9 |
| 22 | 2.4 | 2.3 | 2.1 | 1.9 |

The sera were diluted 1/800

| Week | Mouse 1 | Mouse 2 | Mouse 3 | Mouse 4 |
|---|---|---|---|---|
| Control mice | | | | |
| Immune response against the Hsp70 protein | | | | |
| 2 | 0 | 0 | 0 | 0 |
| 4 | 0 | 0 | 0 | 0 |
| 6 | 0 | 0 | 0 | 0 |
| 8 | 0 | 0 | 0 | 0 |
| 10 | 0 | 0 | 0 | 0 |
| 12 | 0.1 | 0 | 0.3 | 0 |
| 14 | 0.3 | 0.2 | 0.5 | 0.4 |
| 16 | 0.5 | 0.6 | 0.6 | 0.3 |
| 18 | 0.7 | 0.6 | 0.7 | 0.5 |
| 20 | 1 | 0.8 | 0.5 | 1.2 |
| 22 | 1.7 | 1.4 | 0.8 | 1.1 |

The sera were diluted 1/200

EXAMPLE 4

Immunization with Protein Q+BCG in Balb/c Mice

Four Balb/c mice were each injected intraperitoneally with 5 micrograms of protein Q and $10^6$ Colony Forming Units (CFU) of BCG (bacille Calmette-Gu_rin) dissolved in 40 microlitres of PBS. Immunization was effected in three doses, 15 days apart. 15 days after the third immunization, they were administered an inoculum of infective parasites of $10^5$ BCN150 of *L. infantum* by the intracardiac route. Every two weeks, throughout the time of immunization and throughout infection, blood samples were taken from them for testing the degree of humoral response to protein Q. The animals were sacrificed at week 8 after infection.

Table 7 (a and b) shows that the immunized animals respond positively to protein Q starting from the second week and that the response increases progressively until in many cases it reaches values of 400,000. Table 8 shows the difference in parasitic burden between the liver and spleen of the vaccinated and control animals.

TABLE 7

Immune response to protein Q in Balb/c mice immunized with 5 micrograms of protein Q and $10^6$ CFU of BCG
Mice 1, 2, 3, 4 immunized
Mice 5, 6, 7, 8 unimmunized controls
Reaction to protein Q

| week | Mouse 1 | Mouse 2 | Mouse 3 | Mouse 4 | Mouse 5 | Mouse 6 | Mouse 7 | Mouse 8 |
|---|---|---|---|---|---|---|---|---|
| preimmune | 0 | 0 | 0 | 0 | 0 | 0 | 0 | 0 |
| 1st immuniz. | | | | | | | | |
| 1 | 0 | 0.2 | 0.1 | 0 | 0 | 0 | 0 | 0 |
| 2nd immuniz. | | | | | | | | |
| 3 | 0.5 | 0.7 | 0.8 | 0.9 | 0 | 0 | 0 | 0 |
| 3rd immuniz. | | | | | | | | |
| 6 | 1.6 | 2.1 | 2.6 | 2.7 | 0 | 0 | 0 | 0 |
| 7 | 1.8 | 2.3 | 2.4 | 2.1 | 0 | 0 | 0 | 0 |
| 9 | 2.1 | 2.6 | 2.5 | 1.9 | 0 | 0 | 0 | 0 |
| 11 | 2.7 | 2.9 | 3 | 3 | 0 | 0 | 0 | 0 |
| 13 | 3 | 3 | 3 | 3 | 0 | 0 | 0 | 0 | the number 3 is equivalent to overflow in the measurement system
the sera were taken at the beginning of each of the the weeks indicated
the 1st immunization was effected on day 0, the 2nd on day 15 and the third on day 30.

TABLE 8

Parasitic burden in the liver and spleen of Balb/c mice vaccinated with protein Q subcutaneously + $10^6$ of BCG. 8 weeks after infection, the parasitic burden was measured by optical microscopy of tissue impressions by measuring different fields containing 7000 nucleated cells. The parasitic burden is represented as the quantity of parasites per milligram of tissue, having previously calculated that 1 parasite per 1000 nucleated cells is equivalent to an approximate quantity of 210 paraasites per milligram of tissue.
RPB = reduction of parasitic burden, %.

| Mouse | Liver | (RPB) | Spleen | (RPB) |
|---|---|---|---|---|
| 1 | 72 | (82%) | 457 | (89%) |
| 2 | 40 | (90%) | 207 | (95%) |
| 3 | 48 | (88%) | n.d. | (100%) |
| 4 | n.d. | (100%) | 90 | (98%) |

| Controls | | |
|---|---|---|
| 4 animals. Mean | 400 ± 15 | 4155 ± 30 | n.d. parasites could not be detected in 5000 nucleated cells.

What is claimed is:

1. A method for the prevention or treatment of visceral leischmaniosis in a human or an animal, comprising administering to a human or an animal in need thereof a pharmaceutical composition comprising the protein having the amino acid sequence of SEQ ID NO:1.

* * * * *

SEQUENCE LISTING

<160> NUMBER OF SEQ ID NOS: 12

<210> SEQ ID NO 1
<211> LENGTH: 412
<212> TYPE: PRT
<213> ORGANISM: Artificial Sequence
<220> FEATURE:
<223> OTHER INFORMATION: Description of Artificial Sequence: Protein Q

<400> SEQUENCE: 1

Met Arg Gly Ser His His His His His His Thr Asp Pro His Ala Ser
 1               5                  10                  15

Ser Asn Asn Asn Asn Asn Asn Asn Asn Asn Leu Gly Ile Glu Gly
            20                  25                  30

Arg Pro Leu Ala Thr Pro Arg Ser Ala Lys Lys Ala Val Arg Lys Ser
        35                  40                  45

Gly Ser Lys Ser Ala Lys Cys Gly Leu Ile Phe Pro Val Gly Arg Val

```
            50                  55                  60
Gly Gly Met Met Arg Arg Gly Gln Tyr Ala Arg Arg Ile Gly Ala Ser
 65                  70                  75                  80

Gly Ala Pro Arg Ile Ser Glu Phe Ser Val Lys Ala Ala Gln Ser
                 85                  90                  95

Gly Lys Lys Arg Cys Arg Leu Asn Pro Arg Thr Val Met Leu Ala Ala
                100                 105                 110

Arg His Asp Asp Ile Gly Thr Leu Leu Lys Asn Val Thr Leu Ser
                115                 120                 125

His Ser Gly Val Val Pro Asn Ile Ser Lys Ala Met Ala Lys Lys Lys
130                 135                 140

Gly Gly Lys Lys Gly Lys Ala Thr Pro Ser Ala Pro Glu Phe Gly Ser
145                 150                 155                 160

Ser Arg Pro Met Ser Thr Lys Tyr Leu Ala Ala Tyr Ala Leu Ala Ser
                165                 170                 175

Leu Ser Lys Ala Ser Pro Ser Gln Ala Asp Val Glu Ala Ile Cys Lys
                180                 185                 190

Ala Val His Ile Asp Val Asp Gln Ala Thr Leu Ala Phe Val Met Glu
                195                 200                 205

Ser Val Thr Gly Arg Asp Val Ala Thr Leu Ile Ala Glu Gly Ala Ala
210                 215                 220

Lys Met Ser Ala Met Pro Ala Ala Ser Ser Gly Ala Ala Ala Gly Val
225                 230                 235                 240

Thr Ala Ser Ala Ala Gly Asp Ala Ala Pro Ala Ala Ala Ala Ala Lys
                245                 250                 255

Lys Asp Glu Pro Glu Glu Glu Ala Asp Asp Met Gly Pro Ser Arg
                260                 265                 270

Val Asp Pro Met Gln Tyr Leu Ala Ala Tyr Ala Leu Val Ala Leu Ser
                275                 280                 285

Gly Lys Thr Pro Ser Lys Ala Asp Val Gln Ala Val Leu Lys Ala Ala
                290                 295                 300

Gly Val Ala Val Asp Ala Ser Arg Val Asp Ala Val Phe Gln Glu Val
305                 310                 315                 320

Glu Gly Lys Ser Phe Asp Ala Leu Val Ala Glu Gly Arg Thr Lys Leu
                325                 330                 335

Val Gly Ser Gly Ser Ala Ala Pro Gly Ala Val Ser Thr Ala Gly
                340                 345                 350

Ala Gly Ala Gly Ala Val Ala Glu Ala Lys Lys Glu Glu Pro Glu Glu
                355                 360                 365

Glu Glu Ala Asp Asp Asp Met Gly Pro Val Asp Leu Gln Pro Ala Ala
                370                 375                 380

Ala Ala Pro Ala Ala Pro Ser Ala Ala Ala Lys Glu Glu Pro Glu Glu
385                 390                 395                 400

Ser Asp Glu Asp Asp Phe Gly Met Gly Gly Leu Phe
                405                 410

<210> SEQ ID NO 2
<211> LENGTH: 1436
<212> TYPE: DNA
<213> ORGANISM: Artificial Sequence
<220> FEATURE:
<223> OTHER INFORMATION: Description of Artificial Sequence: DNA
      encoding protein Q

<400> SEQUENCE: 2
```

-continued

```
atgagaggat ctcaccacca ccaccaccac acggatccgc atgcgagctc gaacaacaac      60
aacaataaca ataacaacaa cctcgggatc gagggaaggc ctttagctac tcctcgcagc     120
gccaagaagg ccgtccgcaa gagcggctcc aagtccgcga aatgtggtct gatcttcccg     180
gtgggccgcg tcggcgggat gatgcgccgc ggccagtacg ctcgccgcat cggtgcctct     240
ggcgccccca ggatttcaga attctccgtg aaggcggccg cgcagagcgg aagaagcgg      300 tgccgcctga acccgcgcac cgtgatgctg ccgcgcgcc acgacgacga catcggcacg      360
cttctgaaga acgtgacctt gtctcacagc ggcgttgtgc cgaacatcag caaggcgatg     420
gcaaagaaga agggcggcaa gaagggcaag gcgacaccga gcgcgcccga attcggatcc     480
tctagaccca tgtccaccaa gtacctcgcc gcgtacgctc tggcctccct gagcaaggcg     540
tccccgtctc aggcggacgt ggaggctatc tgcaaggccg tccacatcga cgtcgaccag     600
gccaccctcg cctttgtgat ggagagcgtt acgggacgcg acgtggccac cctgatcgcg     660
gagggcgccg cgaagatgag cgcgatgccg gcggccagct ctggtgccgc tgctggcgtc     720
actgcttccg ctgcgggtga tgcggctccg gctgccgccg ccgcgaagaa ggacgagccc     780
gaggaggagg ccgacgacga catgggcccc tctagagtcg accccatgca gtacctcgcc     840
gcgtacgccc tcgtggcgct gtctggcaag acgccgtcga aggcggacgt tcaggctgtc     900
ctgaaggccg ccggcgttgc cgtggatgcc tcccgcgtgg atgccgtctt ccaggaggtg     960
gagggcaaga gcttcgatgc gctggtggcc gagggccgca cgaagctggt gggctctggc    1020
tctgccgctc ctgctggcgc tgtctccact gctggtgccg cgctggcgc ggtggccgag     1080 gcgaagaagg aggagcccga ggaggaggag gccgatgatg acatgggccc cgtcgacctg    1140
cagcccgccg ctgccgcgcc ggccgcccct agcgccgctg ccaaggagga gccgaggag     1200 agcgacgagg acgacttcgg catgggcggt ctcttctaag cgactcgcca tctcttagcc    1260
tccttgtggt gcgcttgagg tgctctcgct ctgcttctcc ttgcagtgtt ggctgactct    1320
ggcgggtatg tgccgtcgca ttacacccac ctctcccacc cctttgccct acgcgctcgc    1380
atgcgcaatc cgtgaatcat cgagggaagt ctctctgggt ggcagtgggt aagctt        1436
```

<210> SEQ ID NO 3
<211> LENGTH: 383
<212> TYPE: PRT
<213> ORGANISM: Artificial Sequence
<220> FEATURE:
<223> OTHER INFORMATION: Description of Artificial Sequence: Protein Q

<400> SEQUENCE: 3

```
Ile Glu Gly Arg Pro Leu Ala Thr Pro Arg Ser Ala Lys Lys Ala Val
1               5                   10                  15

Arg Lys Ser Gly Ser Lys Ser Ala Lys Cys Gly Leu Ile Phe Pro Val
            20                  25                  30

Gly Arg Val Gly Gly Met Met Arg Arg Gly Gln Tyr Ala Arg Arg Ile
        35                  40                  45

Gly Ala Ser Gly Ala Pro Arg Ile Ser Glu Phe Ser Val Lys Ala Ala
    50                  55                  60

Ala Gln Ser Gly Lys Lys Arg Cys Arg Leu Asn Pro Arg Thr Val Met
65                  70                  75                  80

Leu Ala Ala Arg His Asp Asp Ile Gly Thr Leu Leu Lys Asn Val
                85                  90                  95

Thr Leu Ser His Ser Gly Val Val Pro Asn Ile Ser Lys Ala Met Ala
            100                 105                 110
```

```
Lys Lys Lys Gly Gly Lys Lys Gly Lys Ala Thr Pro Ser Ala Pro Glu
        115                 120                 125

Phe Gly Ser Ser Arg Pro Met Ser Thr Lys Tyr Leu Ala Ala Tyr Ala
    130                 135                 140

Leu Ala Ser Leu Ser Lys Ala Ser Pro Ser Gln Ala Asp Val Glu Ala
145                 150                 155                 160

Ile Cys Lys Ala Val His Ile Asp Val Asp Gln Ala Thr Leu Ala Phe
                165                 170                 175

Val Met Glu Ser Val Thr Gly Arg Asp Val Ala Thr Leu Ile Ala Glu
            180                 185                 190

Gly Ala Ala Lys Met Ser Ala Met Pro Ala Ala Ser Ser Gly Ala Ala
            195                 200                 205

Ala Gly Val Thr Ala Ser Ala Ala Gly Asp Ala Ala Pro Ala Ala Ala
        210                 215                 220

Ala Ala Lys Lys Asp Glu Pro Glu Glu Glu Ala Asp Asp Met Gly
225                 230                 235                 240

Pro Ser Arg Val Asp Pro Met Gln Tyr Leu Ala Ala Tyr Ala Leu Val
                245                 250                 255

Ala Leu Ser Gly Lys Thr Pro Ser Lys Ala Asp Val Gln Ala Val Leu
            260                 265                 270

Lys Ala Ala Gly Val Ala Val Asp Ala Ser Arg Val Asp Ala Val Phe
        275                 280                 285

Gln Glu Val Glu Gly Lys Ser Phe Asp Ala Leu Val Ala Glu Gly Arg
290                 295                 300

Thr Lys Leu Val Gly Ser Gly Ser Ala Ala Pro Ala Gly Ala Val Ser
305                 310                 315                 320

Thr Ala Gly Ala Gly Ala Gly Ala Val Ala Glu Ala Lys Lys Glu Glu
                325                 330                 335

Pro Glu Glu Glu Glu Ala Asp Asp Met Gly Pro Val Asp Leu Gln
                340                 345                 350

Pro Ala Ala Ala Ala Pro Ala Ala Pro Ser Ala Ala Ala Lys Glu Glu
            355                 360                 365

Pro Glu Glu Ser Asp Glu Asp Asp Phe Gly Met Gly Gly Leu Phe
    370                 375                 380

<210> SEQ ID NO 4
<211> LENGTH: 27
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 4
cctttagcta ctcctcgcag cgccaag                                        27

<210> SEQ ID NO 5
<211> LENGTH: 27
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 5
cctgggggcg ccagaggcac cgatgcg                                        27

<210> SEQ ID NO 6
```

```
<211> LENGTH: 26
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 6
gaattctccg taaggcggcc gcgcag                                       26

<210> SEQ ID NO 7
<211> LENGTH: 30
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 7
gaattcgggc gcgctcggtg tcgccttgcc                                   30

<210> SEQ ID NO 8
<211> LENGTH: 30
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 8
gtcgacccca tgcagtacct cgccgcgtac                                   30

<210> SEQ ID NO 9
<211> LENGTH: 30
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 9
gtcgacgggg cccatgtcat catcggcctc                                   30

<210> SEQ ID NO 10
<211> LENGTH: 32
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 10
tctagacccg ccatgtcgtc gtcttcctcg cc                                32

<210> SEQ ID NO 11
<211> LENGTH: 29
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 11
tctagagggg ccatgtcgtc gtcggcctc                                    29

<210> SEQ ID NO 12
<211> LENGTH: 30
```

-continued

```
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 12
ctgcagcccg ccgctgccgc gccggccgcc                                30
```